United States Patent
Tao et al.

(10) Patent No.: US 10,222,372 B2
(45) Date of Patent: Mar. 5, 2019

(54) ANTIBIOTIC SUSCEPTIBILITY TESTING VIA PLASMONIC IMAGING AND TRACKING

(71) Applicants: Nongjian Tao, Fountain Hills, AZ (US); Karan Syal, Jalandhar (IN)

(72) Inventors: Nongjian Tao, Fountain Hills, AZ (US); Karan Syal, Jalandhar (IN)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 187 days.

(21) Appl. No.: 15/223,365

(22) Filed: Jul. 29, 2016

(65) Prior Publication Data
US 2017/0045514 A1    Feb. 16, 2017

Related U.S. Application Data

(60) Provisional application No. 62/200,500, filed on Aug. 3, 2015.

(51) Int. Cl.
    *G01N 33/543*    (2006.01)
    *G01N 33/569*    (2006.01)

(52) U.S. Cl.
    CPC . *G01N 33/56916* (2013.01); *G01N 33/54373* (2013.01); *G01N 33/56911* (2013.01)

(58) Field of Classification Search
    None
    See application file for complete search history.

(56) References Cited

PUBLICATIONS

Kee et al., Plasmonic nanohole arrays for monitoring growth of bacteria and antibitoic susceptibility test, Sensors and Actuators B 182, pp. 576-583, available online Mar. 23, 2013. (Year: 2013).*

Aghayee, S. et al. Combination of fluorescence microscopy and nanomotion detection to characterize bacteria. J. Mol. Recognit. 2013, 26, 590-5.

Ai, Y. et al. Separation of *Escherichia coli* bacteria from peripheral blood mononuclear cells using standing surface acoustic waves. Anal. Chem. 2013, 85, 9126-34.

Angus, D. C. et al. Severe Sepsis and Septic Shock. N. Engl. J. Med. 2013, 369, 840-851.

Barenfanger, J. et al. Clinical and financial benefits of rapid bacterial identification and antimicrobial susceptibility testing. J. Clin. Microbiol. 1999, 37, 1415-1418.

(Continued)

*Primary Examiner* — Rebecca L Martinez
(74) *Attorney, Agent, or Firm* — George A. Leone; Citadel Patent Law

(57)    ABSTRACT

A rapid antibiotic susceptibility test (AST) based on the detection and quantification of the movement of single bacterial cells with a plasmonic imaging and tracking (PIT) technology. The PIT-based AST detects changes in the metabolic activity of the bacterial cells long before cell replication, and allows rapid AST for both cultivable and non-cultivable strains. PIT tracks 3D movement with sub-nanometer resolution and millisecond temporal resolution. PIT also allows simultaneous measurement of the binding kinetic constants of antibiotics and bacterial metabolic state after the introduction of antibiotics.

12 Claims, 21 Drawing Sheets

(56) References Cited

PUBLICATIONS

Berger, A. et al. Robustness and plasticity of metabolic pathway flux among uropathogenic isolates of Pseudomonas aeruginosa. PLoS One. 2014, 9, e88368.
Berke, A. P. et al. Hydrodynamic attraction of swimming microorganisms by surfaces. Phys. Rev. Lett. 2008, 101, 1-4.
Besant, J. D. et al. Rapid electrochemical phenotypic profiling of antibiotic-resistant bacteria. Lab Chip. 2015, 15, 2799-2807.
Besser, R. E. et al. *Escherichia coli* 0157:H7 Gastroenteritis and the Hemolytic Uremic Syndrome: An Emerging Infectious Disease. Annu. Rev. Med. 1999, 50, 355-367.
Boedicker, J. Q. et al. Detecting bacteria and determining their susceptibility to antibiotics by stochastic confinement in nanoliter droplets using plug-based microfluidics. Lab Chip. 2008, 8, 1265-1272.
Bradley, D. E. A function of Pseudomonas aeruginosa PAO polar pili: twitching motility. Can. J. Microbiol. 1980, 26, 146-154.
Burrows, L. L. et al. Molecular characterization of the Pseudomonas lipopolysaccharide gene cluster. Mol. Microbiol. 1996, 22, 481-495.
Butler, M. T. et al. Cell density and mobility protect swarming bacteria against antibiotics. Proc. Natl. Acad. Aci. U. S. A. 2010, 107, 3776-81.
Buzatu, D. a. et al. An integrated flow cytometry-based for real-time, high sensitivity bacterial detection and identification. PLoS One. 2014, 9, e94254.
Centers of Disease and Control Prevention. Antibiotic Resistance Threats in the United States, 2013; U.S. Department of Health and Human Services: Washington DC, 2013.
Chattopadhyay, S. et al. Swimming efficiency of bacterium *Escherichia coli*. Proc. Natl. Acad. Sci. U. S. A. 2006, 103, 13712-13717.
Chen, C. H. et al. Antimicrobial Susceptibility Testing Using High Surface-to-Volume Ratio Microchannels. Anal. Chem. 2010, 82, 1012-1019.
Choi, J. et al. Rapid Antibiotic Susceptibility Testing by Tracking Single Cell Growth in a Microfluidic Agarose Channel System. Lab Chip. 2013, 13, 280-287.
Choi, J. et al. A Rapid Antimicrobial Susceptibility Test Based on Single-Cell Morphological Analysis. Sci. Transl. Med. 2014, 6, 267ra174.
Chotinantakul, K. et al. Advanced Amperometric Respiration Assay for Antimicrobial Susceptibility Testing. Anal. Chem. 86, 10315-10322 (2014).
Churski, K. et al. Rapid screening of antibiotic toxicity in an automated microdroplet system. Lab Chip 12, 1629 (2012).
Dalgaard, P. et al. Estimation of Bacterial Growth Rates from Turbidimetric and Viable Count Data. Int. J. Food Microbiol. 1994, 23, 391-404.
Daniels, R. Surviving the First Hours in Sepsis: Getting the Basics Right (an Intensivist's Perspective). J. Antimicrob. Chemother. 2011, 66, 11-23.
Dasgupta, N. et al. A four-tiered transcriptional regulatory circuit controls flagellar biogenesis in Pseudomonas aeruginos. Mol. Microbiol. 2003, 50, 809-824.
Daugelavičius, R. et al. Stages of Polymyxin B Interaction with the *Escherichia coli* Cell Envelope. Antimicrob. Agents Chemother. 2000, 44, 2969-2978.
Ertl, P. et al. Rapid antibiotic susceptibility testing via electrochemical measurement of ferricyanide reduction by *Escherichia coli* and *Clostridium sporogenes*. Anal. Chem. 2000, 72, 4957-4964 (2000).
Flores-Mireles, A. L. et al. Urinary Tract Infections: Epidemiology, Mechanisms of Infection and Treatment Options. Nat. Rev. Microbiol. 2015, 13, 269-284.
Fredborg, M. et al. Real-time optical antimicrobial susceptibility testing. J. Clin. Microbiol. 51, 2047-2053 (2013).
Frymier, P. D. et al. Three-dimensional tracking of motile bacteria near a solid planar surface. Proc. Natl. Acad. Sci. U. S. A. 1995, 92, 6195-6199.
Gfeller, K. Y. et al. Rapid Biosensor for Detection of Antibiotic-Selective Growth of *Escherichia coli*. 2005, 71, 2626-2631.
Hancock, R. E W. The end of an era? Nat. Rev. Drug Discov. 2006, 6, 28-28.
Harbarth, S. et al. Inappropriate Initial Antimicrobial Therapy and Its Effect on Survival in a Clinical Trial of Immunomodulating Therapy for Severe Sepsis. Am. J. Med. 2003, 115, 529-535.
Reller, L. B. et al. Antimicrobial susceptibility testing: a review of general principles and contemporary practices. Clin. Infect. Dis. 2009, 49, 1749-1755.
Kasas, S. et al. Detecting Nanoscale Vibrations as Signature of Life. Proc. Natl. Acad. Sci. U. S. A. 2015, 112, 378-381.
King, A. Recommendations for Susceptibility Tests on Fastidious Organisms and Those Requiring Special Handling. J. Antimicrob. Chemother. 2001, 48, 77-80.
Kinnunen, P. et al. Monitoring the Growth and Drug Susceptibility of Individual Bacteria Using Asynchronous Magnetic Bead Rotation Sensors. Biosens. Bioelectron. 2011, 26, 2751-2755.
Kohler, T. et al. Swarming of Pseudomonas aeruginosa is dependent on cell-to-cell signaling and requires flagella and pili. J. Bacteriol. 2000, 182, 5990-5996.
Kumar, R et al. Quorum sensing is necessary for the virulence of Pseudomonas aeruginosa during urinary tract Infection. Kidney Int. 2009, 76, 286-292.
Kunin, C. M. et al. Novel screening method for urine cultures using a filter paper dilution system. J. Clin. Microbiol. 2000, 38, 1187-1190.
Kuo, S. C. et al. Roles of cheY and cheZ gene products in controlling flagellar rotation in bacterial chemotaxis of *Escherichia coli* J. Bacteriol. 1987, 169, 1307-14.
Lane, M. C. et al. Role of Motility in the Colonization of Uropathogenic *Escherichia coli* in the Urinary Tract Role of Motility in the Colonization of Uropathogenic *Escherichia coli* in the Urinary Tract. 2005, 73, 7644-7656.
Linares, J. F. et al. Antibiotics as intermicrobial signaling agents. Proc. Natl. Acad. Sci. U. S. A. 2006, 103, 19484-19489.
Lissandrello, C. et al. Nanomechanical Motion of *Escherichia coli* Adhered to a Surface. Appl. Phys. Left. 2014, 105, 113701.
Longo, G. et al. Rapid detection of bacterial resistance to antibiotics using AFM cantilevers as nanomechanical sensors. Nat. Nanotechnol. 2013, 8, 522-526.
Lu, Y et al. Single Cell Antimicrobial Susceptibility Testing by Confined Microchannels and Electrokinetic Loading. Anal. Chem. 2013, 85, 3971-3976.
Maki, N. et al. Motility and chemotaxis of filamentous cells of *Escherichia coli*. J. Bacteriol. 2000, 182, 4337-4342.
Mallik, R. et al. Cytoplasmic dynein functions as a gear in response to load. Nature. 2004, 427, 649-652.
Mann, T.S. et al. Antibiotic susceptibility testing at a screen-printed carbon electrode array. Anal. Chem. 2008, 80, 843-848.
Mattick, J. S. Type IV pili and twitching motility. Annu. Rev. Microbiol. 2002, 56, 289-314.
Merz, A.J. et al. Pilus retraction powers bacterial twitching motility. Nature. 2000, 407, 98-102.
Metzger, S. et al. Rapid Simultaneous Identification and Quantitation of *Staphylococcus aureus* and Pseudomonas Aeruginosa Directly from Bronchoalveolar Lavage Specimens Using Automated Microscopy. Diagn. Microbiol. Infect. Dis. 2014, 79, 160-165.
Mignot, T. et al. Evidence that focal adhesion complexes power bacterial gliding motility. Science. 2007, 315, 853-856.
Mittal, R. et al. Correlation between serogroup, in vitro biofilm formation and elaboration of virulence factors by uropathogenic Pseudomonas aeruginosa. FEMS Immunol. Med. Microbiol. 2010, 58, 237-243.
Mittal, R. et al. Urinary tract infections caused by Pseudomonas aeruginosa: A minireview. J. Infect. Public Health, 2009, 2, 101-111.
Mohan, R. et al. A multiplexed microfluidic platform for rapid antibiotic susceptibility testing. Biosens. Bioelectron. 2013, 49, 118-125.
Molaei, M. et al. Failed escape: Solid surfaces prevent tumbling of *Escherichia coli*. Phys. Rev. Lett. 2014, 113, 1-6.
Murray, T. S. et al. Pseudomonas aeruginosa exhibits sliding motility in the absence of type IV pili and flagella. J. Bacteriol. 2008, 190, 2700-2708.

(56) References Cited

PUBLICATIONS

Nan, X. et al. Observation of individual microtubule motor steps in living cells with endocytosed quantum dots. J. Phys. Chem. B. 2005, 109, 24220-24224.

Nunn, D. et al. Products of three accessory genes, pilB, pilC, and pilD, are required for biogenesis of Pseudomonas aeruginosa pili. J. Bacteriol. 1990, 172, 2911-2919.

O'Toole, G. A. et al. Flagellar and twitching motility are necessary for Pseudomonas aeruginosa biofilm development. Mol Microbiol, 1998, 30, 295-304.

Ocampo, P. S. et al. Antagonism between Bacteriostatic and Bactericidal Antibiotics Is Prevalent. Antimicrob. Agents Chemother. 2014, 58, 4573-4582.

Parry, B. R. et al. The Bacterial Cytoplasm Has Glass-like Properties and Is Fluidized by Metabolic Activity. Cell 2014,156, 183-194.

Price, C. S. et al. Rapid antibiotic susceptibility phenotypic characterization of *Staphylococcus aureus* using automated microscopy of small numbers of cells. J. Microbiol. Methods. 2014, 98, 50-58.

Rai, A. K. et al. Molecular adaptations allow dynein to generate large collective forces inside cells. Cell. 2013, 152, 172-182.

Rashid, M. H. et al. Inorganic polyphosphate is needed for swimming, swarming, and twitching motilities of Pseudomonas aeruginosa. Proc. Natl. Acad. Sci. U. S. A. 2000, 97, 4885-4890.

Reck-Peterson, S. L et al. Single-Molecule Analysis of Dynein Processivity and Stepping Behavior. Cell, 2006, 126, 335-348.

Shan, X. et al. Imaging the Electrocatalytic Activity of Single Nanoparticles. Nat. Nanotechnol. 2012, 7, 668-672.

Shan, X. et al. Detection of Charges and Molecules with Self-Assembled Nano-Oscillators. Nano Lett. 2014, 14, 4151-4157.

Shi, W. et al. Focal adhesion: getting a grasp on myxobacterial gliding Iron-sulfur clusters as oxygen-responsive. Nature Chem Biol. 3, 205-206 (2007).

Sinn, I. et al. Asynchronous magnetic bead rotation microviscometer for rapid, sensitive, and label-free studies of bacterial growth and drug sensitivity. Anal. Chem. 2012, 84, 5250-6.

Sivanandan, S. et al. Choice and Duration of Antimicrobial Therapy for Neonatal Sepsis and Meningitis. Int. J. Pediatr. 2011, 1-9.

Sochacki, K. et al. Real-time attack on single *Escherichia coli* cells by the human antimicrobial peptide LL-37. Proc. Natl. Acad. Sci. U. S. A. 2011, 108, E77-81.

Sokolov, A. et al. Reduction of viscosity in suspension of swimming bacteria. Phys. Rev. Lett. 2009, 103, 148101.

Song, L. et al. Nanoscopic Vibrations of Bacteria with Different Cell-Wall Properties Adhering to Surfaces under Flow and Static Conditions. ACS Nano. 2014, 8, 8457-8467.

Syal, K. et al. Plasmonic Imaging of Protein Interactions with Single Bacterial Cells. Biosens. Bioelectron. 2015, 63, 131-137.

Taylor, B. L. et al. Reversal of flagellar rotation in monotrichous and peritrichous bacteria: generation of changes in direction. J. Bacteriol. 1974,119, 640-642.

Tielen, P. et al. Genotypic and phenotypic characterization of Pseudomonas aeruginosa isolates from urinary tract infections. Int. J. Med. Microbiol. 2011, 301, 282-292.

Topp, S. et al. Guiding bacteria with small molecules and RNA. J. Am. Chem. Soc. 2007, 129, 6807-6811.

Touhami, A. et al. Temperature dependence of minD oscillation in *Escherichia coli*: Running hot and fast. J. Bacteriol. 2006,188, 7661-7667.

Visca, P. et al. Epidemiological typing of uropathogenic Pseudomonas aeruginosa strains from hospitalized patients. J. Hosp. Infect. 1991, 19, 153-165.

Wang, S. et al. Label-Free Imaging, Detection, and Mass Measurement of Single Viruses by Surface Plasmon Resonance. Proc. Natl. Acad. Sci. U. S. A. 2010, 107, 16028-16032.

Wang, W. et al. Single Cells and Intracellular Processes Studied by a Plasmonic-Based Electrochemical ImpedanceMicroscopy. Nat. Chem. 2011, 3, 249-255.

Wang, W. et al. Label-Free Measuring and Mapping of Binding Kinetics of Membrane Proteins in Single Living Cells. Nat. Chem. 2012, 4, 846-873.

Wang, X. et al. Fluorescent pH-Sensitive Nanoparticles in an Agarose Matrix for Imaging of Bacterial Growth and Metabolism. Angew. Chem., Int. Ed. 2013, 52, 406-409.

Weiss, L. E. et al. Engineering motility as a phenotypic response to LuxI/R-dependent quorum sensing in *Escherichia coli*. Biotechnol. Bioeng. 2008, 100, 1251-1255.

Wiegand, I. et al. Agar and broth dilution methods to determine the minimal inhibitory concentration (MIC) of antimicrobial substances. Nat. Protoc. 2008, 3, 163-175.

Wood, K. A. et al. Pharmacoeconomic Implications of New Therapies in Sepsis. PharmacoEconomics. 2004, 22, 895-906.

Yang, Y. et al. Label-Free Tracking of Single Organelle Transportation in Cells with Nanometer Precision Using a Plasmonic Imaging Technique. Small. 2015, 11, 2878-2884.

Yildiz, A. et al. Kinesin walks hand-over-hand. Science. 2004, 303, 676-678.

Zhang, Y. et al. Membrane Lipid Homeostasis in Bacteria. Nat. Rev. Microbiol. 2008, 6, 222-231.

\* cited by examiner

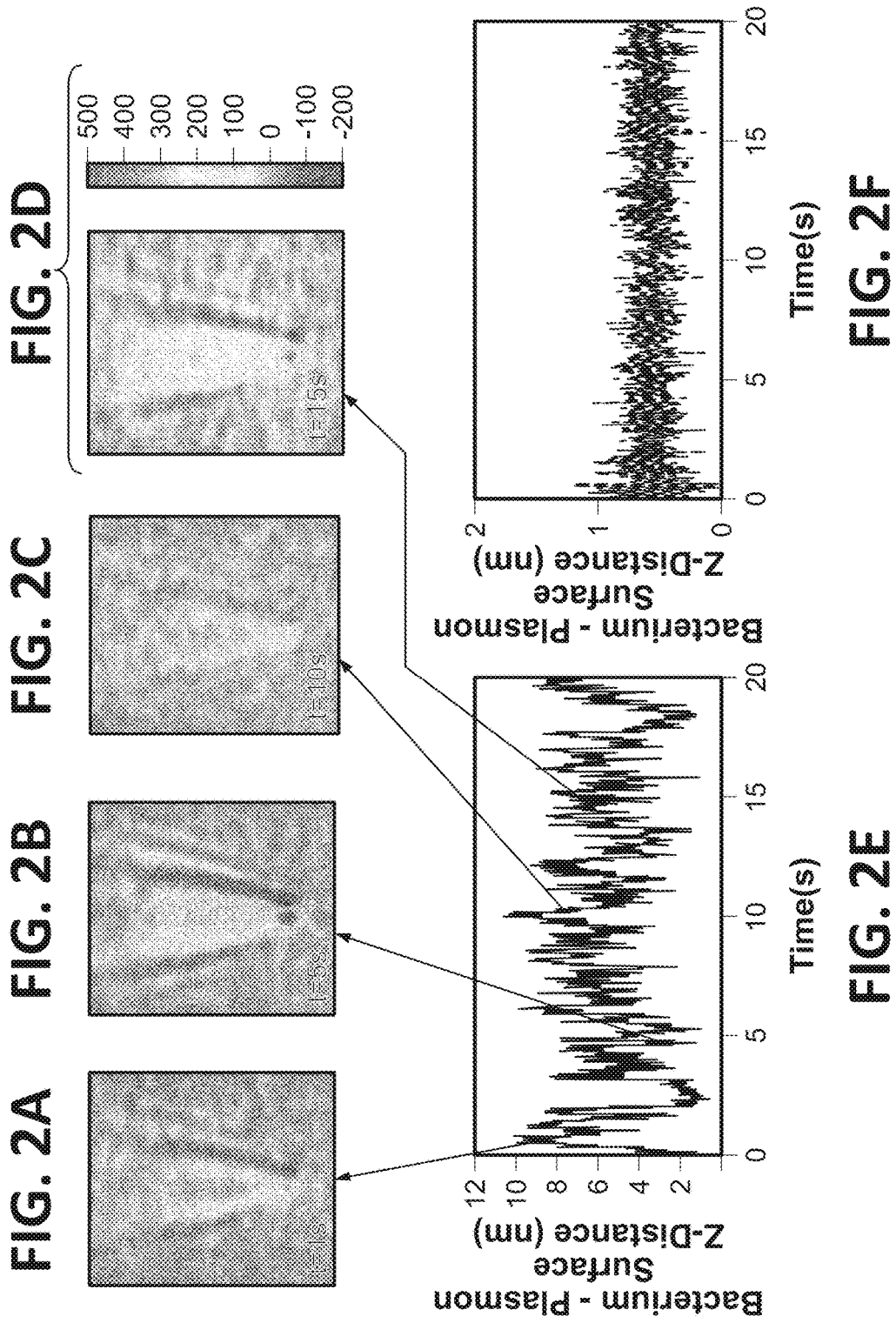

ANTIBIOTIC SUSCEPTIBILITY TESTING VIA PLASMONIC IMAGING AND TRACKING

RELATED APPLICATION

This application claims priority from U.S. application No. 62/200,500 of Nongjian Tao et al., filed Aug. 3, 2015, entitled "ANTIBIOTIC SUSCEPTIBILITY TESTING VIA PLASMONIC IMAGING AND TRACKING." U.S. application No. 62/200,500 is hereby incorporated by reference.

TECHNICAL FIELD

The present invention relates to plasmonic imaging. More particularly, the invention relates to using plasmonic imaging and tracking to carry out antibiotic susceptibility testing related to bacterial infections.

BACKGROUND

Antibiotic-resistant bacterial infections, in acute cases like sepsis and others, result in costing the US billions of dollars in healthcare costs. Estimates vary but have ranged as high as $20 billion in excess direct healthcare costs, with additional costs to society for lost productivity as high as $35 billion a year (2008 dollars)[1]. The prevailing view is that the widespread misuse of antibiotics over the last few decades has allowed bacteria to evolve and develop defenses to neutralize or resist antibiotics. Antibiotic-resistant bacterial infections are spreading at a phenomenal rate and seriously threaten human survival and severely set back medical progress made in the last century[2].

Today, clinical treatment of bacterial infections, especially in acute cases of sepsis, requires multiple steps including (AST). Conventionally, AST requires time-intensive culturing techniques, such as disk-diffusion[3] and broth-dilution[4], which can take up to two days for the bacteria to grow to an appropriate density for clinical assessment. In addition to being time consuming, such AST techniques are limited to cultivable strains of bacteria, leading to delayed administration of appropriate antibiotics that often results in putting patients at risk. Appropriate antibiotic regimens can be unduly delayed, especially for slow-growing and non-cultivable microorganisms. A faster AST is needed to reduce morbidity and mortality rates significantly.

With an increasing clinical demand for AST, multiple methodologies have been developed to characterize antibiotic activity on bacterial metabolism. Examples include the measurement of incremental increases in cell length and number.[5,8] While these approaches have met with some degree of success, they still rely on culturing, which is not universally applicable, especially to non-cultivable microorganisms and anaerobes, new bacterial strains, and slow-growing bacteria.[11]

Techniques, such as magnetic beads[5,6] and optical imaging,[7,8] have been used to measure cell growth by proxy means, recording changes in vibrational amplitude or image intensity. While these alternative techniques meet some requirements, they are still time-consuming and semi-quantitative since they require the bacteria to be grown to high density. More recently, micro-cantilever deflections have been used as metabolic sensors to detect bacterial cell motion.[9,10] In the case of atomic force microscope (AFM) cantilevers, one major disadvantage is the lack of means to differentiate strains and obtain strain-specific susceptibility results. This cantilever approach would be difficult to use when a patient has a polymicrobial infection.

Thus, for humans to win the evolutionary battle between our wits and microbial genes, there is a crucial need for point-of-care technologies that can rapidly generate antibiotic susceptibility profiles of an infecting pathogen, ideally at the earliest stages of disease. Fast generation of antibiotic susceptibility profiles would allow administration of appropriate narrow-spectrum/personalized therapies at the earliest possible stage. Automated, and more universal technologies for antibiotic susceptibility testing (AST), are needed to replace current culture-based approaches. Such a technology would also be applicable to non-cultivable and slow growing microbial species and considerably reduce time required to obtain a susceptibility report.

The present invention overcomes the limitations inherent in the known methods described above. Disclosed herein for the first time is an AST tool based on a plasmonic imaging technology for simultaneous and rapid measurement of the binding kinetics and treatment effects of antibiotics on bacteria in a culture-free environment. This novel AST method can quickly detect antibiotic resistant strains and improve clinical diagnoses.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

The present invention provides a method for plasmonic imaging of binding kinetics of antibodies with bacterial cells. A plasmonic imaging and tracking (PIT) system includes an inverted microscope lens, a light source, a metallic coated slide, a mirror and a detector. Tethering molecules are attached to the metallic coated surface. An analyte is placed on the metallic coated surface and the PIT system is activated to image the analyte. A first set of 3D motion values of the analyte is tracked and an antibiotic is subsequently added to the metallic coated surface. After adding the antibiotic, a second set of 3D motion values of the analyte is tracked. The first and second 3D motion values are compared to determine changes in the 3D motion of the analyte after addition of the antibiotic.

In one aspect, the tethering molecules have an affinity to a bacterial cell under investigation.

In another aspect the tethering molecules comprise antibodies.

In yet another aspect, the analyte is a bacteria selected from the group consisting of *E. coli* and *S. aureus*.

In yet another aspect, the attaching tethering molecules include anti-*E. coli* antibodies.

In yet another aspect, adhesion materials are applied to the metallic coated surface, where the adhesion materials are selected from the group consisting of cell-adhesion promoting substances, poly-lysine, and agar matrix.

In yet another aspect, the computer program for tracking 3D motion values tracking the XY-motion comprises a curve fitting algorithm.

In yet another aspect, the curve-fitting algorithm is selected from the group consisting of Gaussian fitting, elliptical fitting, and spatial averaging.

In yet another aspect, the computer program further comprises a subprogram for extracting an image intensity change from the plasmonic image that is free of noise by transforming the plasmonic image into K-space using Fourier transforms to produce a two-ring image.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 2A-FIG. 2D show images of bacterial z nanomotion revealed by the varying plasmonic image contrast.

FIG. 2E graphically illustrates Z-Distance between bacterium and plasmon surface vs time plot with an average nanomotion magnitude of ~6 nm.

FIG. 2F graphically illustrates Z-Distance between bacterium and plasmon surface plot of a dead bacterial cell (no motion) showing an average motion magnitude of 0.50 nm. Scale bar (2 μm).

Figure 1:
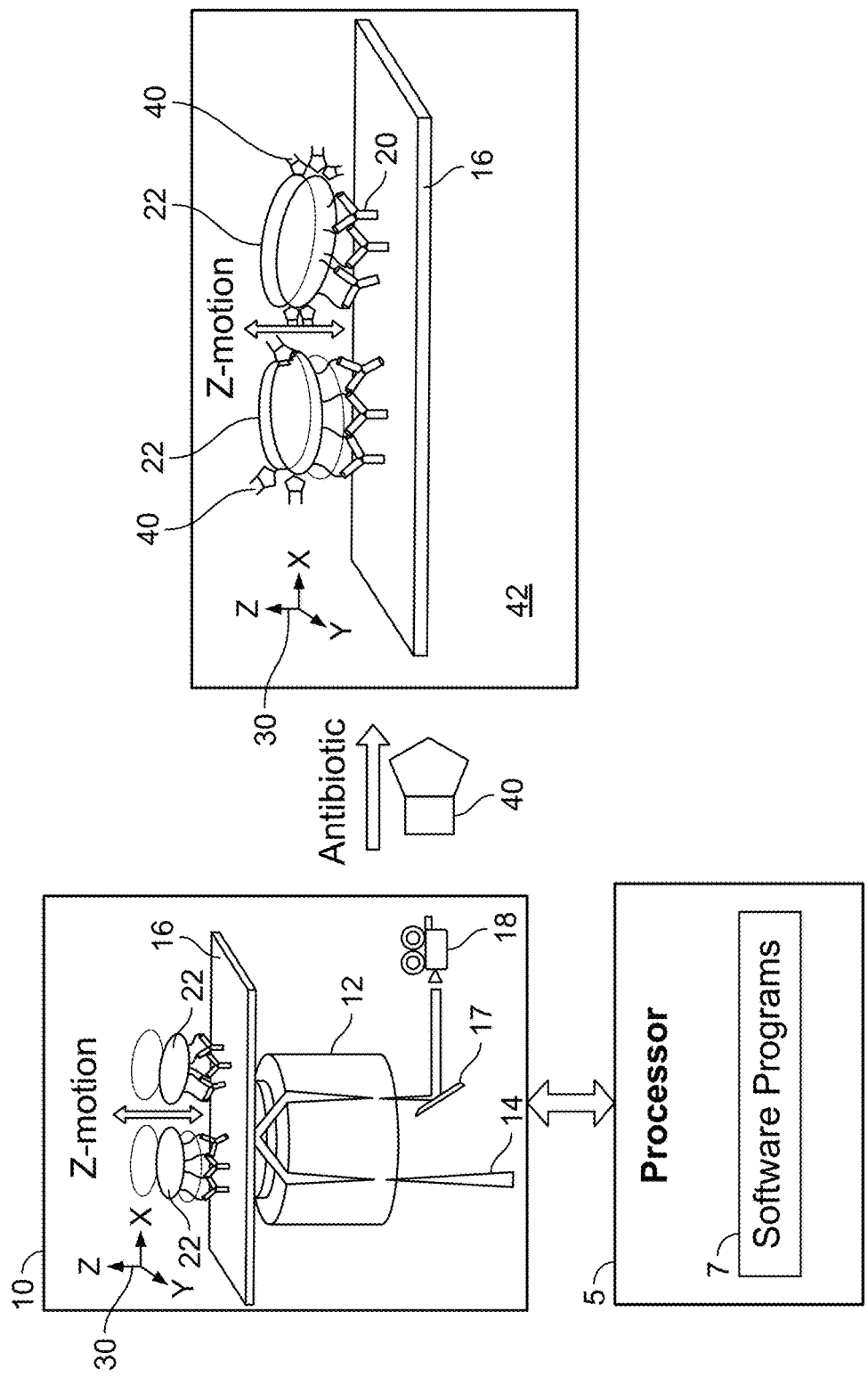
FIG. 1 schematically shows a process flow for plasmonic imaging and tracking (PIT) of bacterial cell metabolic activity-related 3D movement with nanometer resolution.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes an AST testing regime employing plasmonic imaging and tracking. Several features of methods and systems in accordance with example embodiments are set forth and described in the figures. It will be appreciated that methods and systems in accordance with other example embodiments can include additional procedures or features different than those shown in the figures. Example embodiments are described herein with respect to measuring 3D motion of bacterial cells. However, it will be understood that these examples are for the purpose of illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of plasmonic imaging:

As used herein "amplitude" is defined as the standard deviation of the Z-movement for a given period of time.

"AST" as used herein generally refers to antibiotic susceptibility testing. "3D movement" as used herein refers to metabolic activity-related 3D movement.

"PIT" as used herein refers to plasmonic imaging and tracking technology.

As used herein "Z-movement" refers to the relative Z-distance, where the mean bacterium-plasmon surface Z-distance in a given time duration is subtracted from the Z-distance at a given period of time.

Using the methods and systems described herein metabolic activity can be quantified by measuring and analyzing the 3D movement in real time with nanometer resolution. In this way active metabolic movement of a living cell can be distinguished from that of a dead cell, for example. The approach is supported by a recent observation of bacterial metabolism-induced fluctuations by AFM.[9,12] Using plasmonic-based microscopy, simultaneous imaging of mass distribution, electrical impedance, and molecular binding kinetics of single bacterial cells have been demonstrated.[13] Additionally, it has been shown that it is possible to track the 3D movement of single bacterial cells and organelles in 3D with <5 nm spatial resolution and <1 ms temporal resolution. PIT can analyze multiple bacterial cells simultaneously, providing high throughput and quantification of AST with single cell detection and with a capability for statistical analysis of multiple cells.

Compared to traditional culture-based AST techniques, the instant PIT approach monitors 3D movement associated with metabolic activity of bacteria, which is more universal, and can detect metabolic changes due to external metabolites long before cells actually replicate. This strategy enables real-time detection of viable antibiotic-resistant strains (with negligible changes in metabolic activity from patient to laboratory) and offers a significant advantage over the culturing techniques. This approach could be developed into a rapid clinical diagnostic tool (<1 h). One important advantage of PIT over AFM cantilever is the ability to characterize AST on single cells in a mixed bacterial population. In addition, PIT can spatially resolve bacterial cells even in a complex matrix of sera, body fluid samples, etc. This advantage is very critical in translating this technology into a practical solution for testing real patient samples.

Another important innovation is disclosed for simultaneously measuring the binding kinetics of antibiotics to a single bacterial cell and the cellular metabolic effect of antibiotic binding. Previously, surface plasmon resonance has been used to measure only the binding kinetics of molecules to a large number of cells immobilized on a surface. Considering the large cell-cell evolutionary heterogeneity in a microbial population and the importance of the heterogeneity in antibiotic resistance, measuring kinetic parameters for bulk population losses valuable information.

Antibody binding kinetics of single bacterial cells have been measured,[13] and four orders of magnitude cell-to-cell variability has been observed in the equilibrium constant, $K_D$, for a genetically-similar cellular population. Thus, inherent variability of the microbial surface has been demonstrated within a given population. This inherent variability is considered to be even more critical when assessing antibiotic action, which have downstream effects on cellular metabolism, structure, and/or replication. Hence, measuring single cell $K_D$, followed by extrapolation to a bulk population, is considerably more relevant in assessing antimicrobial efficacy. By correlating metabolic activity from 3D bacterial movement and antibiotic binding kinetics, the kinetic and MIC measurements of antibiotics can be combined into a single test using PIT.

To summarize, PIT enables:
a) Rapid and automated AST (<1 h) of antibiotic-resistant bacteria.
b) Universal approach to detect both cultivable and non-cultivable bacteria.
c) Kinetics and MIC measurements of antibiotics in a single step.
d) Single bacterial cell MIC curves in a mixed microbial population as well as complex samples of bacteria in sera, body fluids etc. using imaging capabilities.

Referring now to FIG. 1, a process flow for plasmonic imaging and tracking (PIT) of bacterial cell metabolic activity-related 3D movement with nanometer resolution is schematically shown. A plasmonic imaging and tracking (PIT) system 10 includes an inverted microscope lens 12, a light source 14, a metallic coated slide 16, a mirror and a detector 18. Tethering molecules 20 are attached to the surface of slide 16. The tethering molecules 20 are selected to tether the analyte 22 to the surface. The analyte may comprise a bacterial cell under investigation. In some cases, depending on the affinity of the analyte, antibodies are used to tether the analyte as described below.

A processor 5, such as a computer processor of any suitable type, contains software programs 7 for processing images obtained by the PIT system 10 and for controlling the operation of the PIT system 10. Image processing and quantitative measurements are carried out by algorithms embodied in the software programs as described in more detail hereinbelow.

In one example, imaging and cantilever detection of metabolic fluctuations have been combined using the plasmonic imaging and tracking (PIT) system to track bacterial cell 3D movement associated with metabolic activity and measure the binding kinetics of antibiotics. Clinically-relevant bacterial strains, such as *E. coli* O157:H7 (Gram negative, motile) and *S. aureus* (Gram positive, non-motile), were used to demonstrate the PIT-based AST technology. Plasmonic resonance at the slide surface causes the analyte to move with 3D motion in the X, Y and z planes as referenced to a Cartesian coordinate system 30. The 3D motion is measured before and after the addition of an antibiotic 40. Panel 42 schematically illustrates a reduction in Z-motion after introduction of an antibiotic into the system.

A crucial task for PIT-based AST is to create a robust protocol to tether bacterial cells onto the sensor chip (gold-coated glass slides). The cells must be close to the sensor surface, within a distance of a few hundred nm for optimal PIT sensitivity, and yet the attachment of the cells to the surface cannot be too strong so as not to significantly hinder the 3D movement. In one example, anti-*E. coli* O157:H7 antibodies were used to non-covalently attach bacterial cells. This protocol allows for observation of 3D movement in metabolically active cells that is much greater than Brownian motion (dead cells). Other tethering schemes, including cell-adhesion promoting substances, poly-lysine, and agar matrix,[20] for a mixed population of Gram positive and Gram negative bacteria can also be used.

In one useful embodiment a PIT setup can be built on an optical microscope with a high numerical aperture objective.[62-64] A sensor chip, made of a glass coverslip coated with 47 nm thick gold film, is placed on the microscope sample stage. Light with a wavelength of 680 nm from a super luminescent diode is directed onto the film via the objective. When the incident angle is tuned, surface plasmons are excited on the gold surface, and the reflected light is imaged with a CCD imager. The *E. coli* O157:H7 cells, tethered on a sensor chip via antibody coupling, scatter the surface plasmonic wave, leading to parabolic-shaped patterns in the plasmonic image.[57]

Figure 1A:
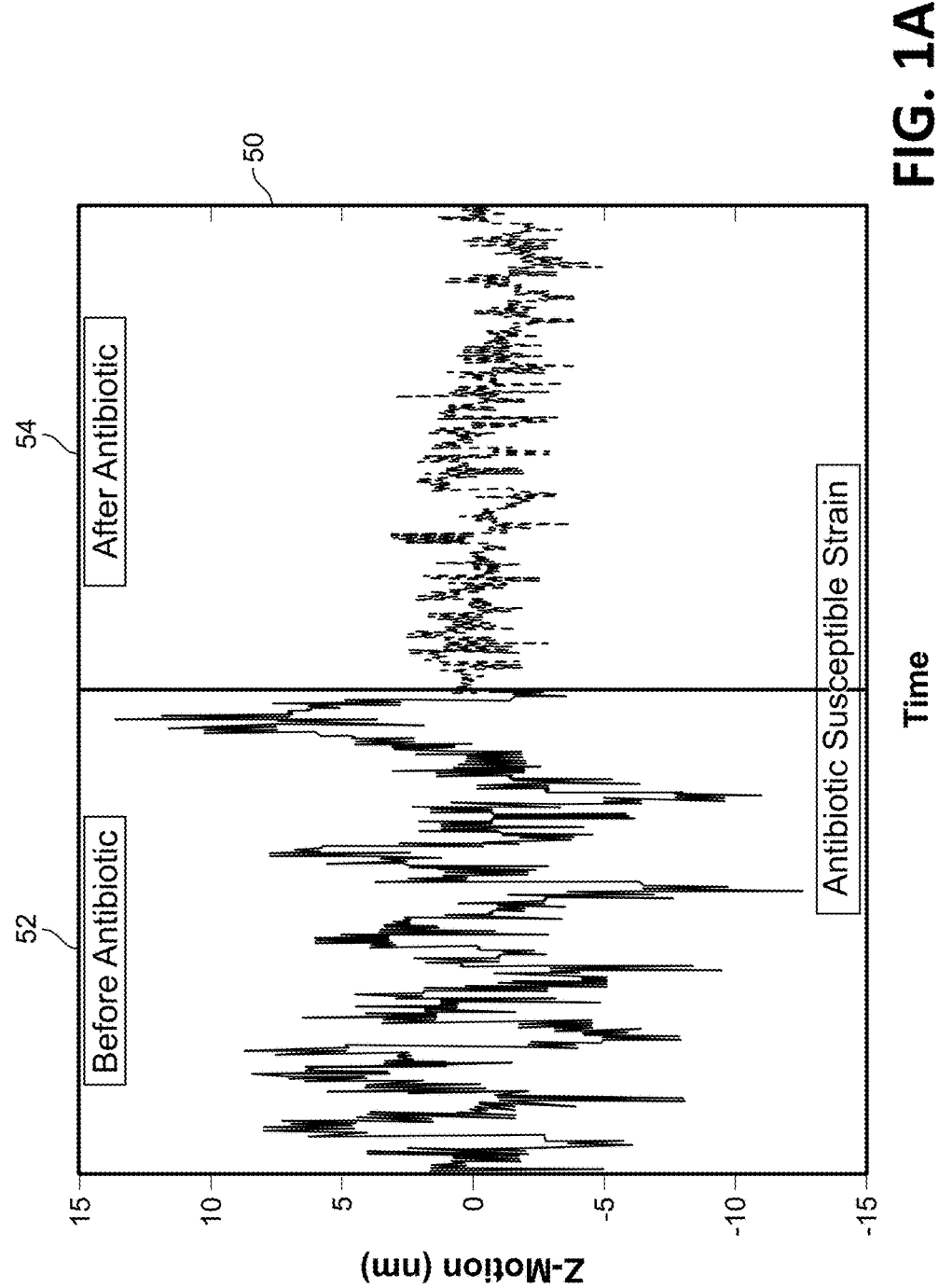
FIG. 1A graphically shows comparative measurements using plasmonic imaging and tracking of bacterial cell metabolic activity-related 3D movement before and after introduction of an antibiotic.

Referring now to FIG. 1A, comparative measurements using plasmonic imaging and tracking of bacterial cell metabolic activity-related 3D movement before and after introduction of an antibiotic is graphically shown. Frame 50 is a graphical representation of Z-motion (nm) on the vertical axis and time in relative units on the horizontal axis. Frame 50 is split into identically scaled left 52 and right 54 temporal frames. The left temporal frame 52 graphically maps Z-motion of an analyte before introduction of an antibiotic. Conversely, right temporal frame 54 graphically maps Z-motion of an analyte after introduction of an antibiotic into the same analyte. A visual comparison of the right and left frames reveals a significant reduction of Z-motion after addition of the antibiotic.

Figure 9A:
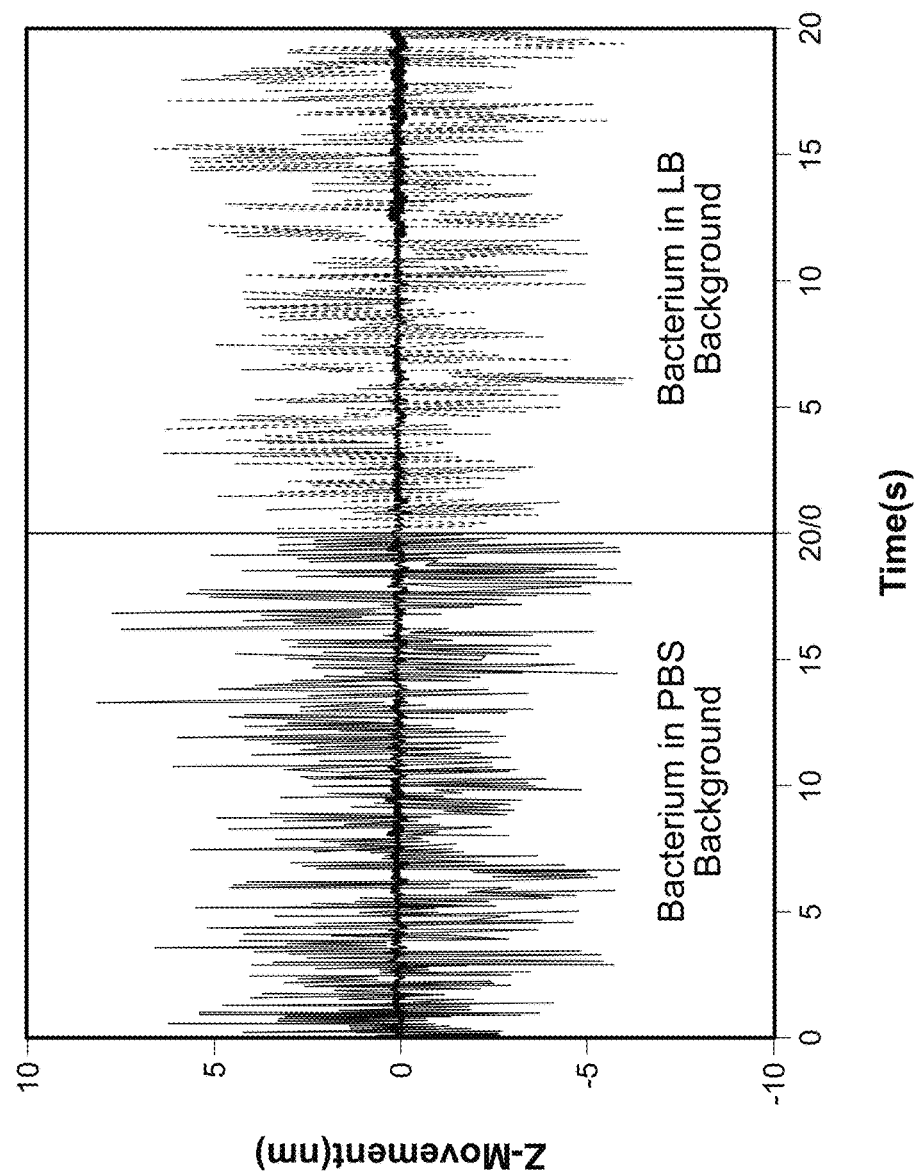
FIG. 9A-FIG. 9C show Z-movement in 1×PBS and LB medium.

Referring now concurrently to FIG. 2A-FIG. 2D, images of bacterial z nanomotion revealed by the varying plasmonic image contrast are shown. The images shown were obtained using 1×PBS as the medium. To ensure that the bacterial cells attached to the surface are metabolically active, the buffer from was changed from 1×PBS to Luria Broth (LB) culture medium and the cells were incubated for approximately 20 min. After incubation in LB, bacterial cells grew, as evident by the elongation of cells detected in the transmission images. Comparisons of the nanomotion of live bacterial cells in 1×PBS and LB revealed similar amplitudes (FIG. 9A).

When analyzed, the motion of the bacterial cells in the transmission and the plasmonic images showed that the transmission image contrast of the bacterial cells appears to be constant, but the plasmonic image contrast fluctuates significantly. To show the contrast fluctuation of the plasmonic image, differential plasmonic images were created by subtracting the lowest contrast image from all of the images. The differential images shown in FIG. 2A-FIG. 2D reveal large fluctuations in the plasmonic image contrast of a bacterial cell at times t=1 s, t=5 s, t=10 s and t=15 s respectively. This image contrast fluctuation is due to the nanomotion of the bacterial cell normal to the z sensor chip (z direction),[65] which is due to the surface plasmon intense evanescent electric field, which decays exponentially from the surface into the bulk solution. Consequently, the scattering of the plasmonic waves by the bacterial cell decreases exponentially with the distance (z) between the cell and the sensor surface. It has been shown previously that the plasmonic image contrast change ($\Delta I/I$) of a particle is related to the distance change ($\Delta z$), by $\Delta I/I = \exp(-\Delta z/95.8\ nm)$.[66]

Referring now to FIG. 2E, Z-Distance between bacterium and plasmon surface vs time plot with an average nanomotion magnitude of ~6 nm is graphically shown where the scale bar represents 2 μm. Using this relation, the nanomotion of the bacterial cell in z direction can be determined. The magnitude of the nanomotion of the bacterial cell above the plasmon surface, is less than 10 nm with an average motion magnitude of ~6 nm, which cannot be detected in the traditional transmission optical image.

Referring now to FIG. 2F, Z-Distance between bacterium and plasmon surface plot of a dead bacterial cell (no motion) showing an average motion magnitude of 0.50 nm is graphically shown where the scale bar represents 2 μm. As a control experiment, the nanomotion of a dead bacterial cell was tracked and observed a much smaller magnitude of nanomotion (~0.50 nm). The data demonstrate the capability of the plasmonic imaging technology for tracking the motion of individual bacterial cells with sub-nanometer precision.

As supported by further evidence shown below, the bacterial nanomotion is related to the bacterial metabolism. For live cells, bacterial metabolism is associated with cytoplasmic membrane transport,[52] cytoplasm fluidity,[57] and modifications of membrane lipid composition in response to environmental changes,[68] all of which can cause micromotion of the cells. In the present system, the bacterial cells are attached to the surface via antibodies, involving soft non-covalent bonds that prevent large-scale motions, but allow nanomotion of the bacterial cells.

EXAMPLE EMBODIMENTS

Tracking Mitochondrion Movement with PIT

Figure 2G:
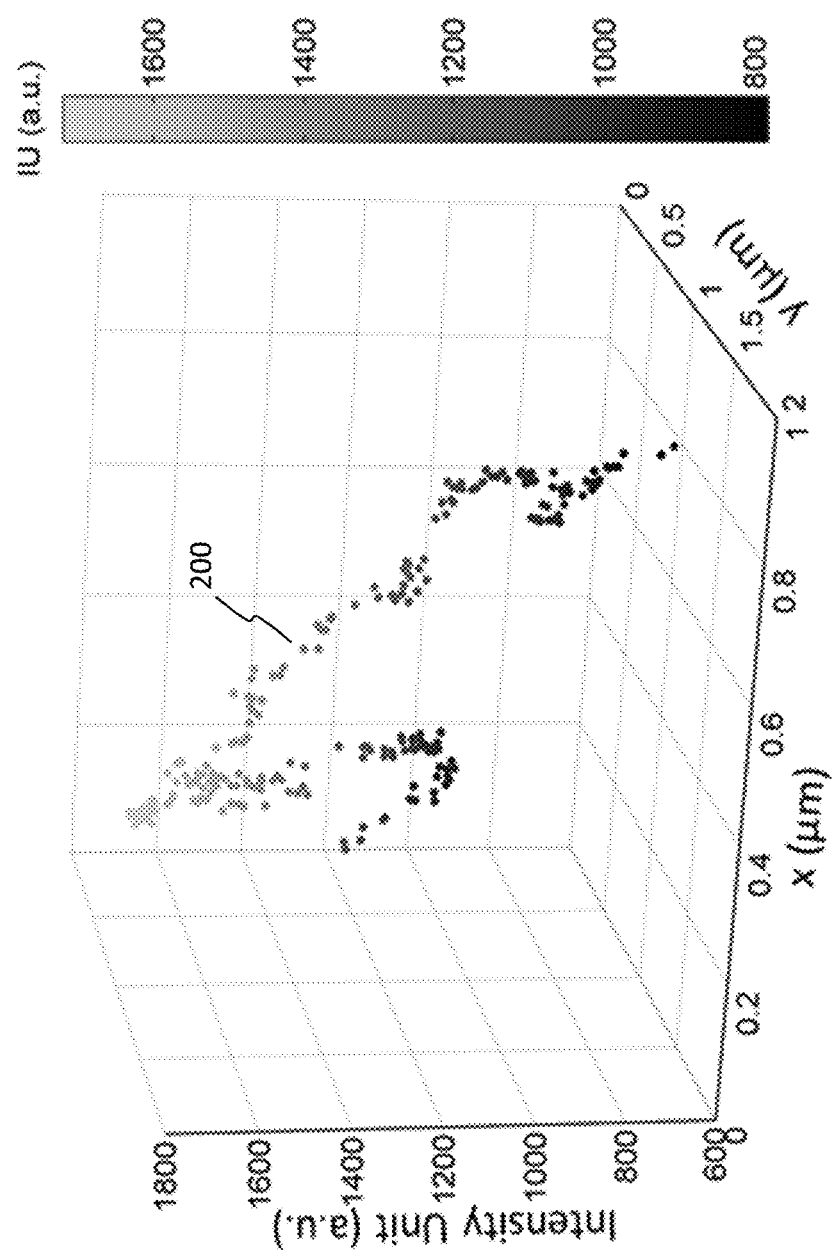
FIG. 2G schematically shows a typical trace of mitochondrion movement tracked using PIT.

Referring now to FIG. 2G, a typical trace of mitochondrion movement in time-lapse plasmonic images is graphically illustrated. A representative trace 200 of mitochondrion movement is tracked using PIT. X and Y translation within 5 nm can be resolved on the horizontal axes, and Z movement is reflected by the image intensity (expressed in a.u.) along the vertical axis. For 3D motion tracking with PIT, a PIT setup on an inverted optical microscope enabling simultaneous capture of plasmonic and impedance images along with additional transmitted, fluorescence TIRF images for validation and additional experiments.[15-18] Using this setup, organelles moving inside a cell with 5 nm spatial resolution and <1 millisecond temporal resolution have been tracked successfully. By fitting the spatial distribution of the plasmonic image intensity with a Gaussian function, a moving organelle in both X and Y directions can be resolved, noting that the movement in z direction is reflected by the plasmonic image intensity (additional details provided below).

3D Movement of Individual Viable and Dead Bacterial Cells

Example 1

Figures 3A, 3B:
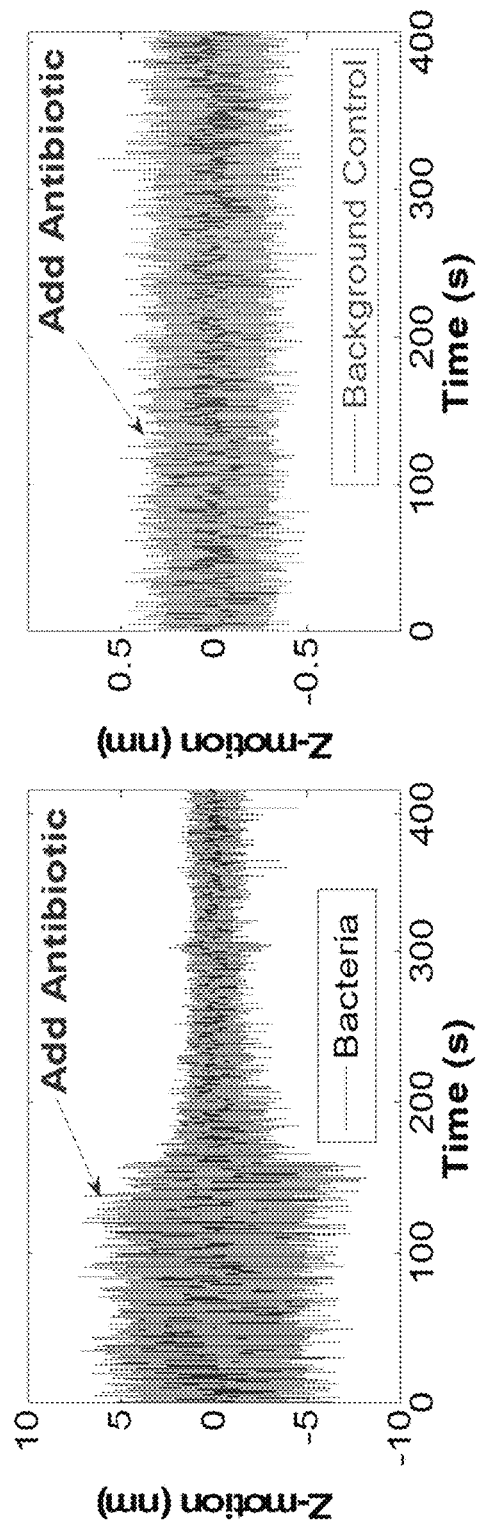
FIG. 3A-FIG. 3D graphically illustrate how Z-motion changes after adding antibiotics.

Referring now concurrently to FIG. 3A-FIG. 3B, Z-motion changes after adding antibiotics are graphically illustrated. In these plots, the vertical axis represents Z-motion in nanometers (nm) and the horizontal axis represents time in seconds (s). Referring now specifically to FIG. 3A, Z-motion of a bacterial cell before and after adding polymyxin B at t=120 s is shown. The large drop in Z-motion associated with the adding of polymyxin B, confirms the feasibility of the invention.

Referring now specifically to FIG. 3B, Z-motion of a background control region, which shows no Z-motion changes after addition of the antibiotic is shown. Z-direction movement tracking is based on the exponential dependence of the plasmonic intensity of an object on its Z movement.[19] Using the procedures and systems disclosed herein, the tracking accuracy in z direction can reach as high as 0.1 nm.[19] To demonstrate this PIT capability for studying bacteria movement, the movement of a living bacterial cell in z direction with concurrent addition of the antibiotic, polymyxin B, at a bactericidal concentration of 75 μg/ml was tracked. Before the addition of polymyxin B, Z-movement decreases from ±5 nm to ±0.5 nm, which is close to the Brownian motion of a dead bacterium. We further validated the metabolic state by culturing and elongating the tethered cell in standard Luria Broth (LB) media before adding the antibiotic. After introducing polymyxin B, subsequent incubation of the bacterium in LB media did not lead to cellular growth, confirming effective antibiotic-mediated killing. This preliminary experiment demonstrates the feasibility of PIT for rapid antibiotic susceptibility testing.

Figure 3C:
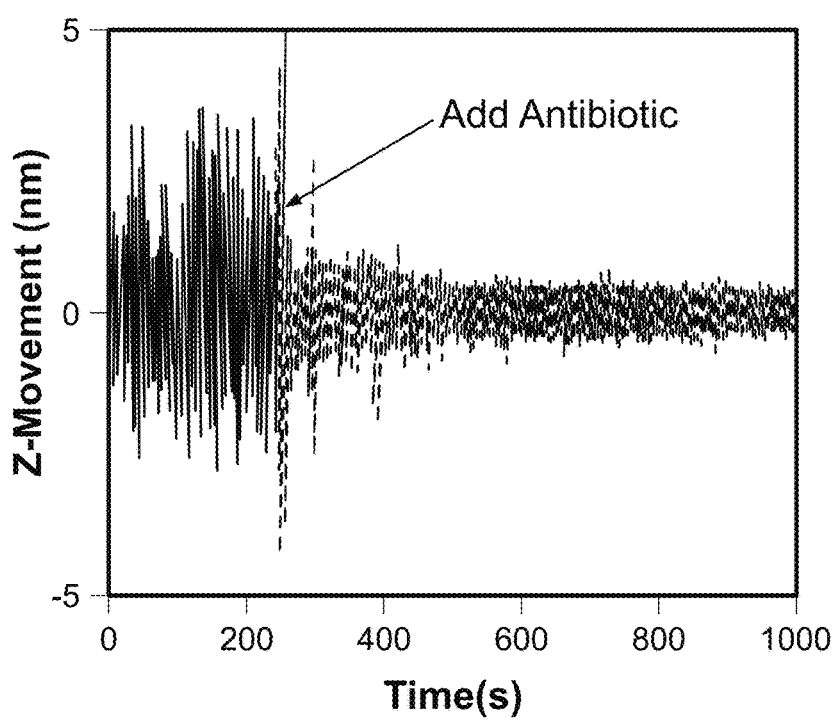
Figure 10:
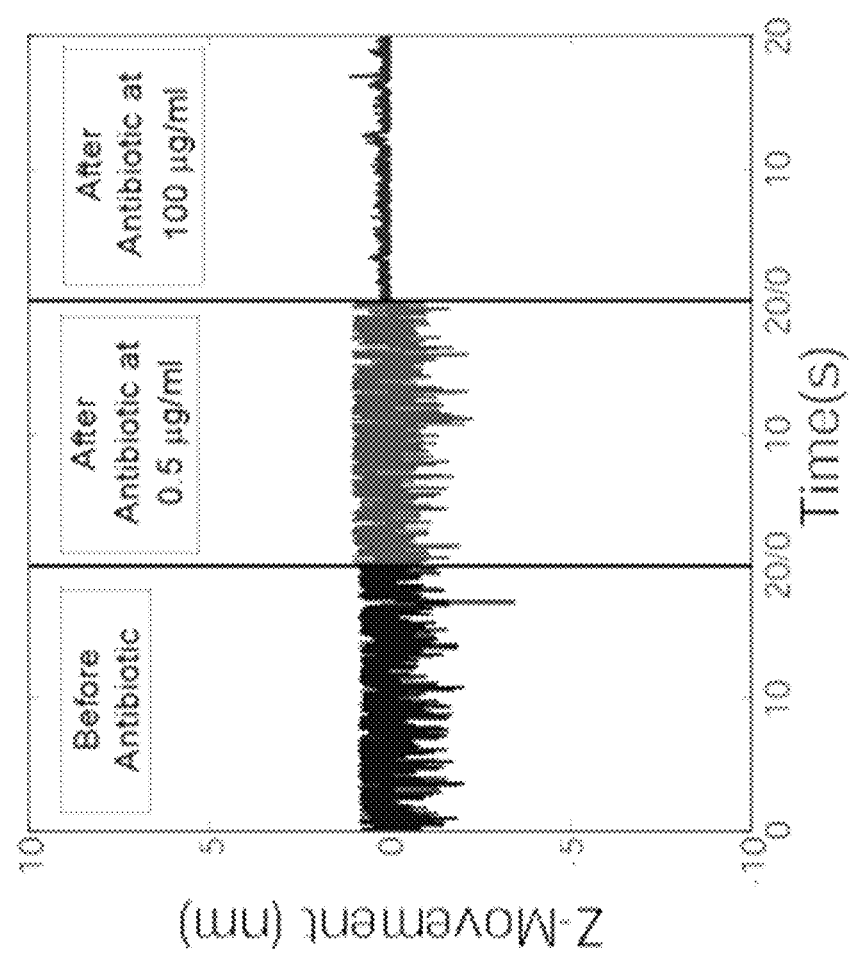
FIG. 10 shows Z-movement in 1×PBS and different concentrations of antibiotic.

Referring now to FIG. 3C the effect of antibiotic polymycin B at a concentration of 500 μg/mL on Z-movement of a bacterial cell is shown. We then studied the effects of antibiotics on the nanomotion of live bacterial cells by adding polymyxin B (PMB) to 1×PBS to reach a final concentration of 500 g/mL. PMB is a bactericidal antibiotic which kills Gram-negative bacteria by permeabilizing the outer membrane.[60] At high concentrations, such as 500 g/mL used in this study, PMB also depolarizes the cytoplasmic membrane, causing ion-permeable pores in the cell envelope.[30] Within a few seconds after adding the antibiotic, there was a marked decrease in the Z-movement of the bacterial cell from about ±3 to about ±1 nm. We further observed that after a few minutes, the bacterial cell Z-movement reached a baseline value of ±0.5 nm. This decrease in bacterial nanomotion can be attributed to bactericidal activity of PMB, which has been observed at a concentration of 20 g/mL.30 We used 25× for the bactericidal concentration in this project to ensure complete loss of cellular viability. Bactericidal activity was also observed by comparing cellular morphology after adding antibiotics, where decreases in bacterial cell length at a high antibiotic concentration were visualized (FIG. 10). The decrease in bacterial cell length has been previously correlated to cell lysis and cell death after the addition of polypeptide antibiotics.[69] We validated the correlation between the decreases in nanomotion and change of the bacterial metabolic state by replacing the antibiotic-containing PBS with LB medium (lacking PMB) on the sensor chip. We observed no further change in the bacterial nanomotion after incubating in LB medium, indicating irreversible loss of metabolic activity after the treatment with PMB. We subsequently collected a small sample volume from the above sensor chip and subjected it to culturing overnight in LB medium. We observed no growth of bacterial cells after overnight incubation, thus confirming bacterial cell death and bactericidal activity of the PMB antibiotic.

Furthermore, we injected antibiotic with a sub-bactericidal concentration (0.5 g/mL), followed by a 5× bactericidal concentration injection. At sub-bactericidal concentrations, we did not observe changes in the nanomotion after 20 min. However, after injecting bactericidal concentrations we observed a significant decrease in nanomotion, which validates the correlation between the decrease in nanomotion and change of the bacterial metabolic state. (FIG. 10). We performed a further control experiment by injecting glucose into the PBS-bacteria mixture. Glucose is a chemo-attractant and represents an energy source for the bacteria.

Figure 3D:
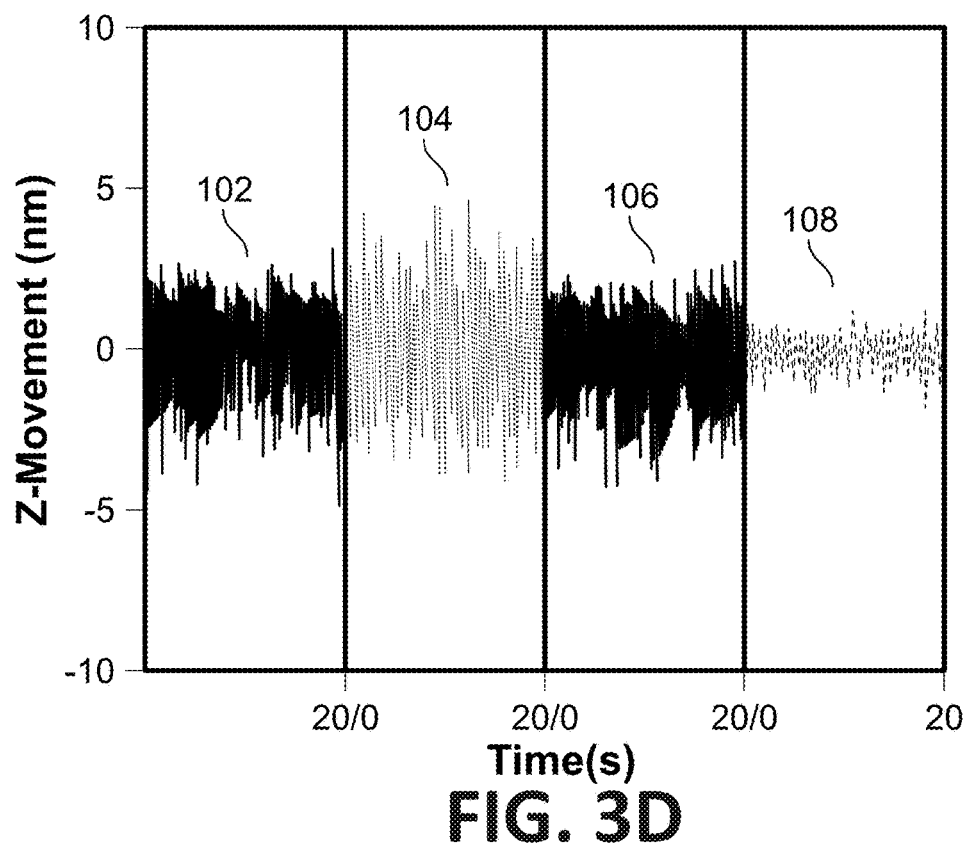
Figure 3E:
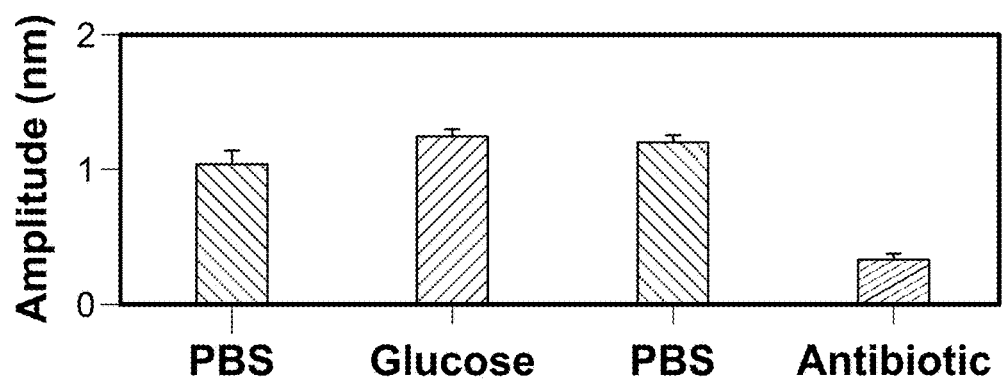
FIG. 3E graphically illustrates amplitude analysis of Z-movements in different media.
Figure 11:
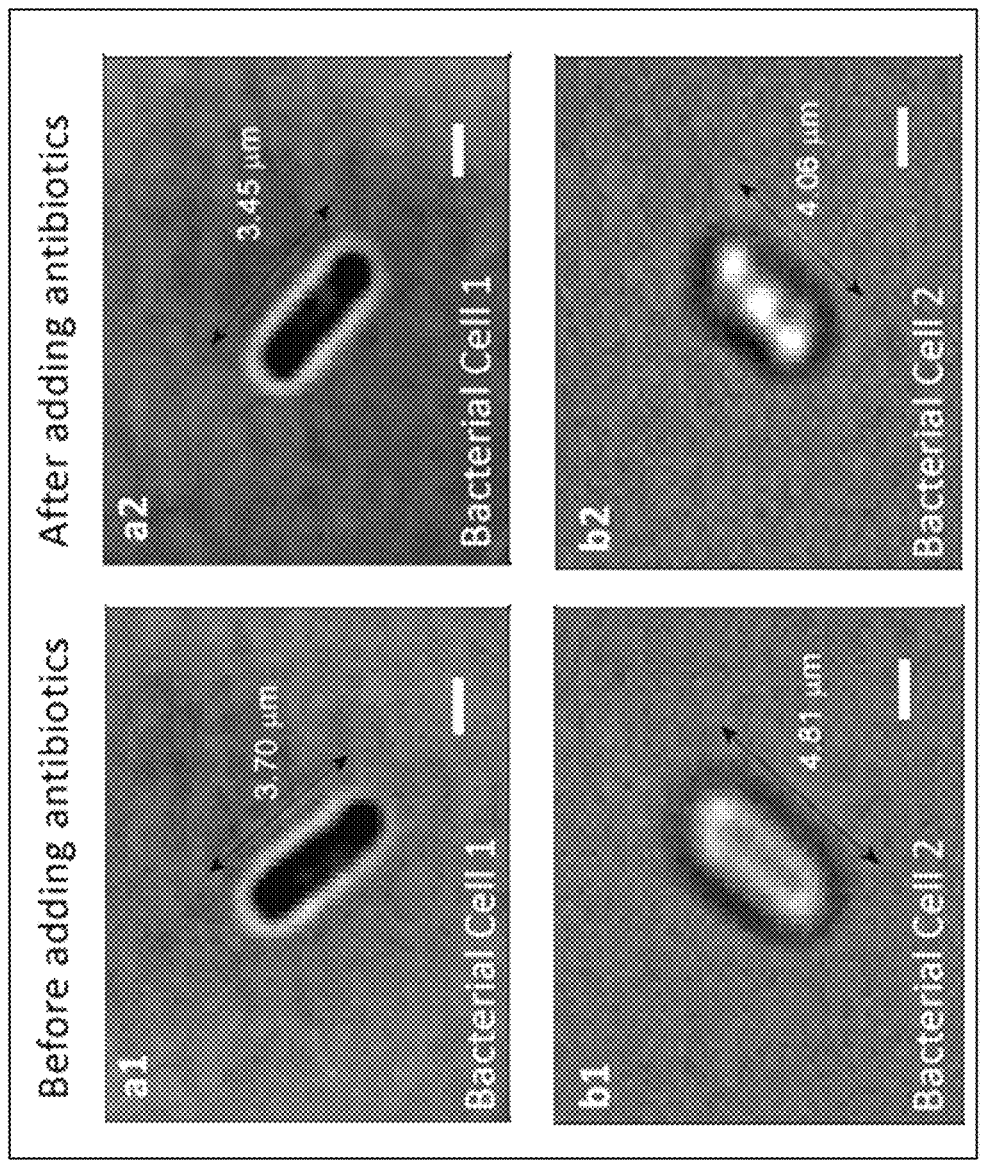
FIG. 11 shows cell death as observed by transmitted images.

Referring now specifically to FIG. 3D, there shown are control experiment data comparing Z-movement in PBS 102 and on injections of 2% glucose 104, 1×PBS 106, and antibiotic 108. After the injection of 2% glucose, the nanomotion of the bacteria increased slightly. After subsequently eliminating glucose in the 1×PBS medium, the amplitude of the nanomotion, measured over 1 s windows for 20 s videos, decreased back to the level prior to the injection of glucose (as shown in FIG. 3E). The positive correlation between glucose injection and Z-movement strongly supports that bacterial cell nanomotion originates from metabolic activity rather than Brownian motion. Conversely, we observed a decrease in bacterial nanomotion only when PMB was added at the bactericidal concentration of 75 g/mL, thus indicating that the decrease in nanomotion is specific to antibiotic action. Antibiotic activity was also observed by the transmitted microscope image, which shows a visible decrease in cell length after the addition of PMB. We subsequently subjected the experimental sample to overnight culturing in LB medium and observed no bacterial growth, thus validating PMB-induced cell death (FIG. 11).

Binding Kinetics of Antibodies with Single Bacterial Cells

Figure 4A:
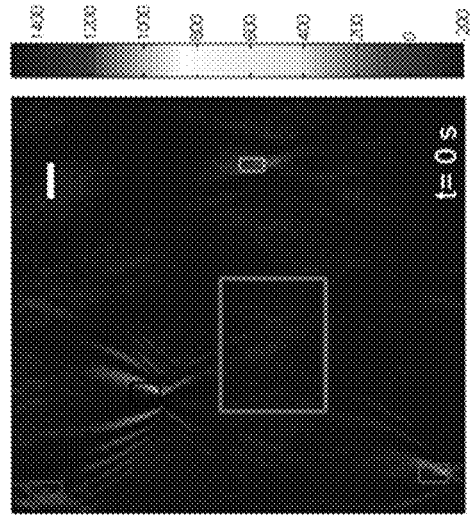
FIG. 4A-FIG. 4D graphically illustrate plasmonic imaging of binding kinetics of antibodies with individual bacterial cells.
Figure 4B:
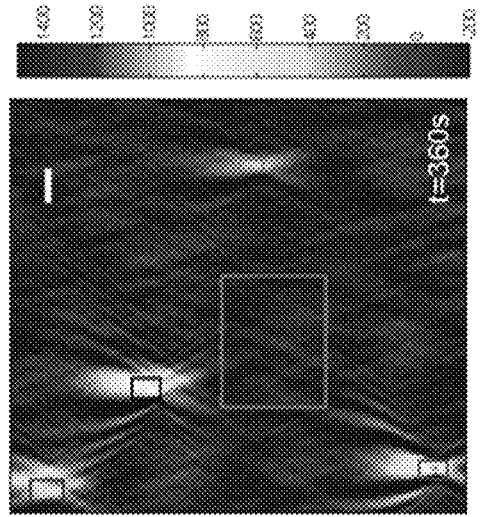
Figure 4C:
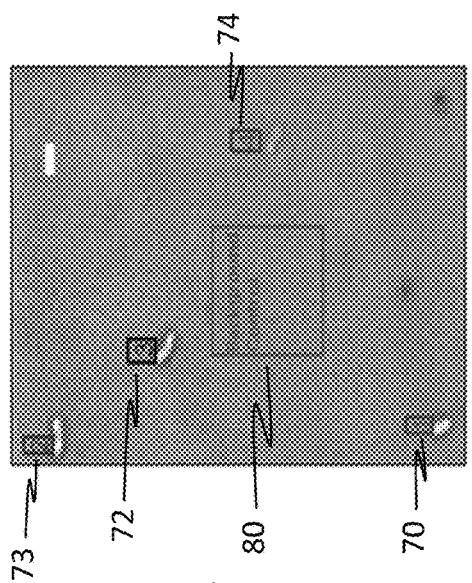
Figure 4D:
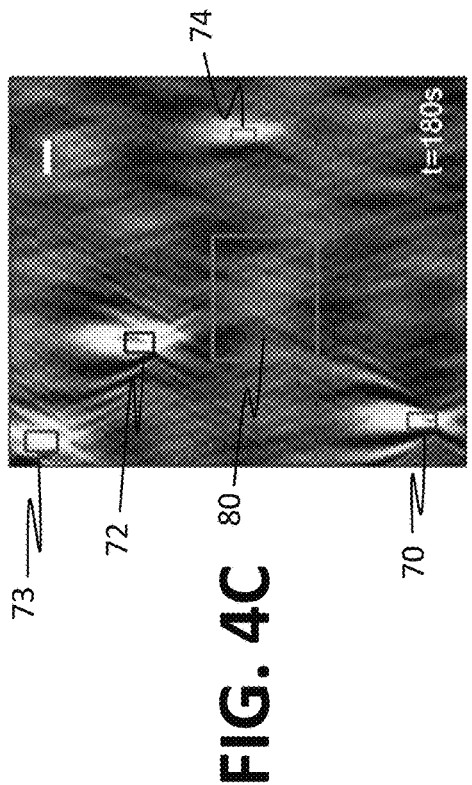

Referring now to FIG. 4, FIG. 4A-FIG. 4D graphically illustrate plasmonic imaging of binding kinetics of antibodies with individual bacterial cells on a scale of 2μ. Referring specifically to FIG. 4A, a bright-field optical image of tethered $E.$ $coli$ O157:H7 cells is shown. Referring specifically to FIG. 4B and FIG. 4C, time-differential plasmonic images captured during different stages of association processes are shown. Referring specifically to FIG. 4D, a time-differential plasmonic image captured during the dissociation process is shown. Within each of FIG. 4A-FIG. 4D specific boxed regions 70, 72, 73, 74 and 80 have been marked. Region 80 is a background control region. The other regions are mapped at various times as shown with reference to FIG. 5 as described below.

Figure 5:
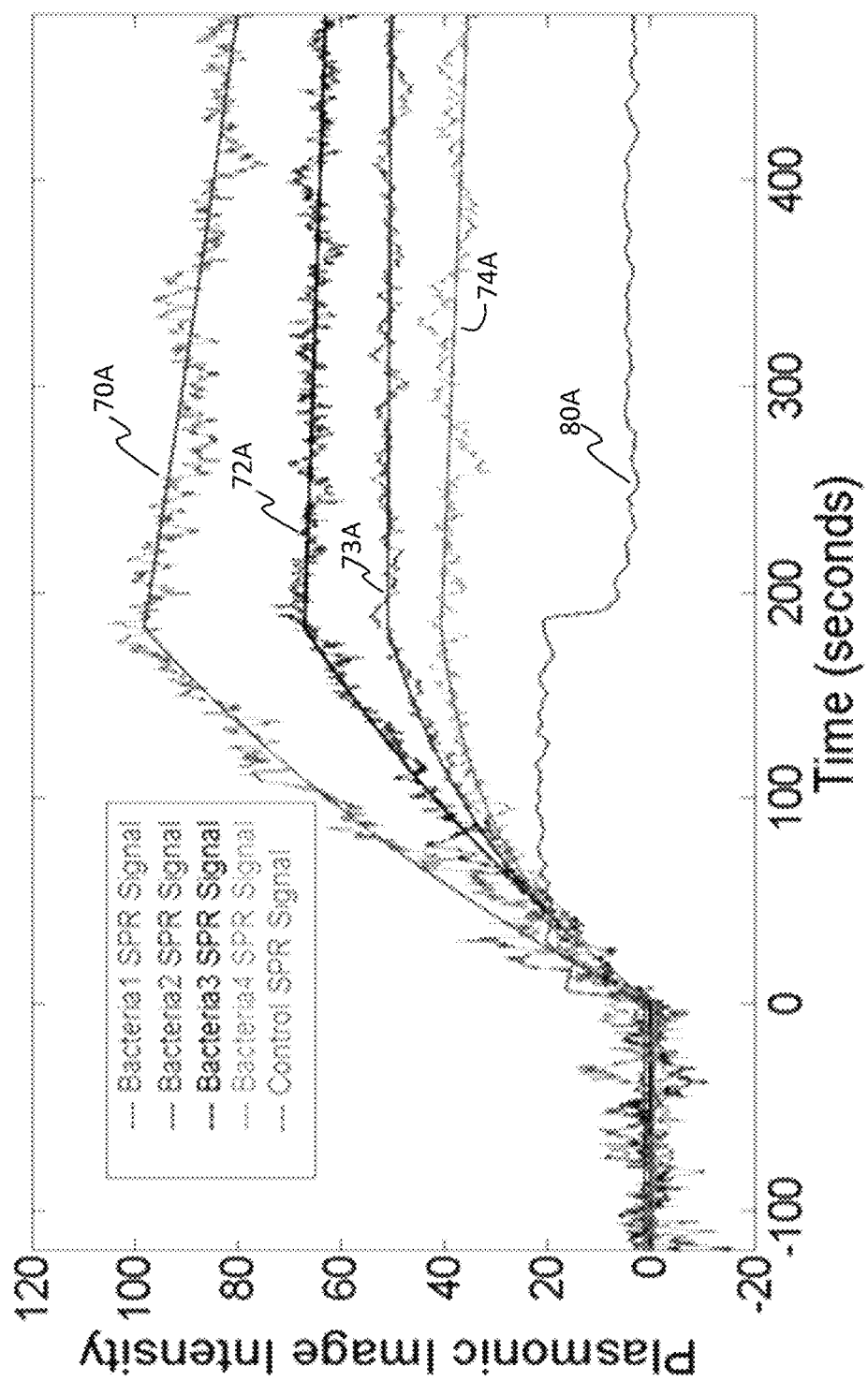
FIG. 5 shows sensorgram signals of single bacterial cells obtained by plotting the image intensity of the colored boxes for bacterial cells and control with time.

Referring now to FIG. 5 sensorgram signals of single bacterial cells obtained by plotting the image intensity of the delineated boxes for bacterial cells and control with time are shown. The sensorgram signals are referenced as 70A, 72A, 73A, 74A and 80A where the leading numerals correspond to regions 70, 72, 73, 74 and 80 respectively. Using PIT, binding of antibody (Ab157) to single $E.$ $coli$ O157:H7 cells was imaged.[13] 1×Phosphate Buffered Saline (1×PBS) was flowed over the bacteria for 2 min to record the baseline plasmonic signal, and then 1×PBS containing 10 μg/ml of Ab157 to observe the antibody association phase. We imaged the binding for 3 min to image the dissociation phase, and then passaged again with 1×PBS. Snapshots of the plasmonic images show a weak contrast in the bacterial region at t=0 s (FIG. 4B), which is attributed to the slight 3D movement of live cells. Snapshots at t=180 s and 360 s (FIGS. 4C and 4D) show an increase in the image contrast of the bacterial cells compared to the background, which is due to the binding of antibody specifically to the bacterial cells. A small image intensity increase in the background control region occurs at t=180 s (FIG. 4C, box 80), which is attributed to bulk refractive index change caused by the change of solution. The images also show differential contrast increase for different cells, demonstrating the cell-to-cell heterogeneity that is washed out in the bulk assay.

Still referring to FIG. 5, the sensorgrams graph image intensity vs. time profiles provide quantitative kinetic information ($k_a$, $k_d$, and $K_D$) of the antibody binding to bacterial cells. Note that the kinetic constants can vary over 4 orders of magnitude,[13] indicating the natural phenotypic diversity in a bacterial population. Superimposed on the sensorgrams is "noise" associated with 3D movement, demonstrating a capability of simultaneous binding kinetics and movement analysis of PIT. The present invention uses an algorithm to analyze and quantify both parameters.

An algorithm, typically structured and operated as a computer program, is advantageously used to quantify active metabolism-induced 3D movement of single cells in real time. The algorithm balances the need of reliability, accuracy, and speed based on the actual imaging quality and operates to track XY-motion and Z-motion. Since the plasmonic image of a bacterial cell is a bright spot with parabolic shape tail due to the scattering of surface plasmons by the cell, the XY-motion of the cell is tracked by detecting the bright spot at the vertex of the parabola with a curve fitting algorithm, such as Gaussian fitting, elliptical fitting, or spatial averaging to find the position of the bacterium.

Figure 6B:
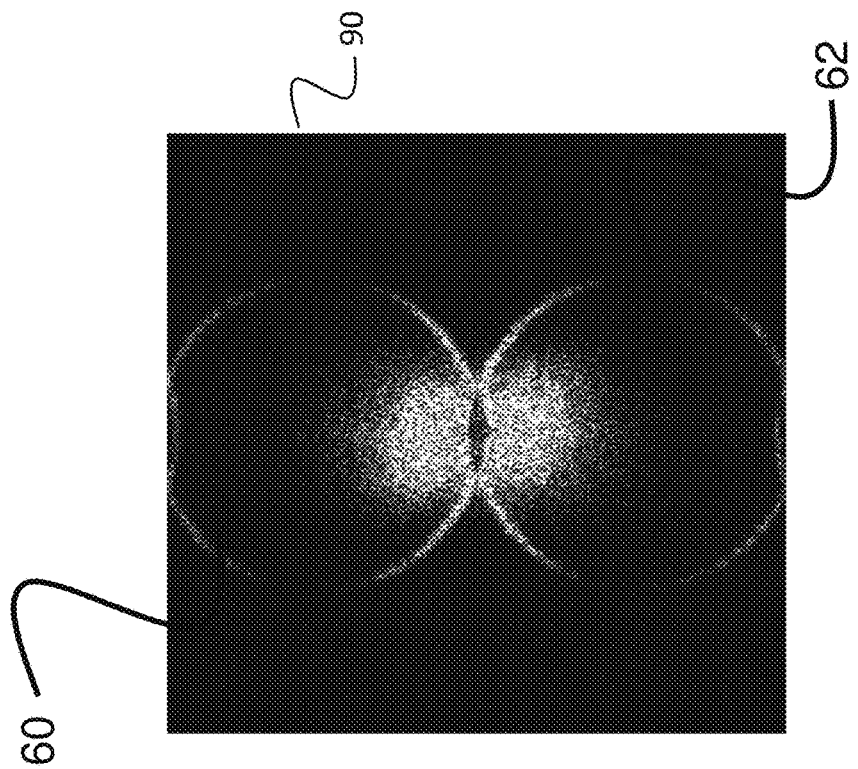
FIG. 6A-FIG. 6B illustrate k-space analysis of PIT images.

In the Z-direction (normal to the sensor surface), the tracking principle relies on the sensitive dependence of the plasmonic imaging intensity on the distance between the cell and sensor surface, which is distinctly different from the XY motion tracking. A second computer-run algorithm operates to extract the image intensity change that is immune of noise. One such useful algorithm transforms the image into k-space (or Fourier space), which is a two ring pattern 90 as shown in FIG. 6B. The overall intensity of the rings in k-space is immune to spatial noises.

Generation of image processing tools allows fast and efficient 3D tracking of multiple bacterial cells simultaneously. A possible challenge of this task is to identify two or more bacterial cells that are physically close to each other. One approach is to distinguish such events from uncorrelated 3D movement. In other words, two closely spaced cells would have an uncorrelated 3D movement. Another solution to this problem is to optimize the number of bacterial cells on the sensor surface to minimize the likelihood of such events. It is believed that as long as such events are rare, they will not affect conclusion of AST.

Figure 6A:

Referring now to FIG. 6A-FIG. 6B, k-space analysis of PIT images is illustrated. Specifically, FIG. 6A shows a PIT image of the bacteria visible as V-shaped patterns in real space. FIG. 6B shows a corresponding PIT image in k-space presenting two distinct rings 60, 62, from which the image intensity of bacterial cells can be extracted.

Referring now to FIG. 7A-7F, Z-movement of individual bacterial cells before and after antibiotic treatment (FIG. 7A, FIG. 7C and FIG. 7E) and PSD of Z-movement of individual bacterial cells before and after antibiotic treatment (FIG. 7B, FIG. 7D and FIG. 7F) is shown.

Figure 7A:
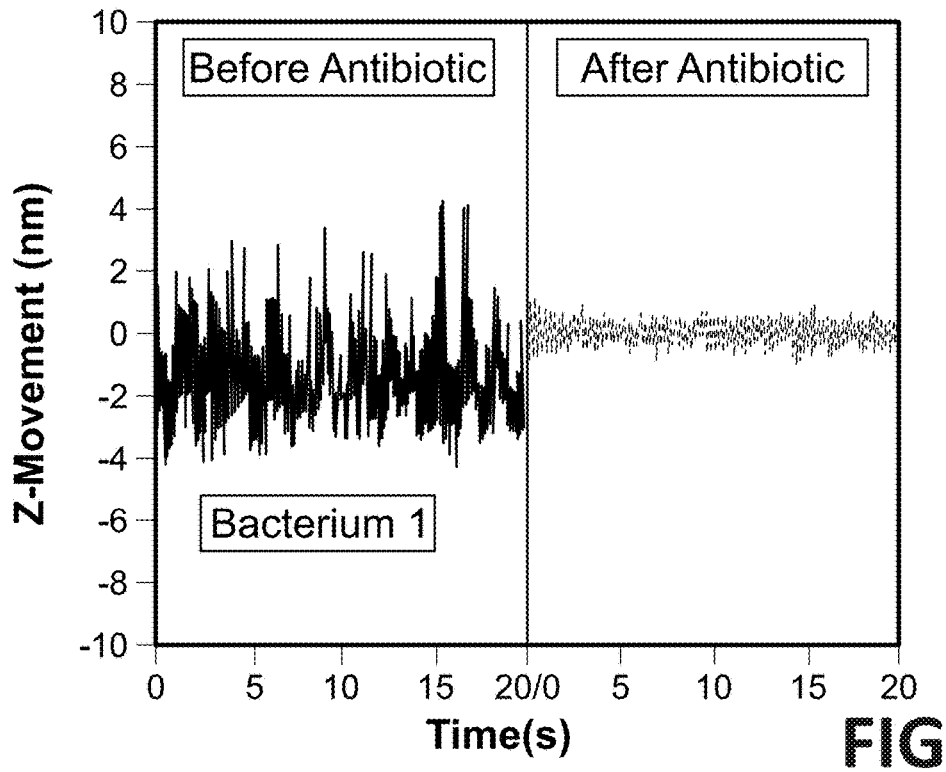
FIG. 7A-7F, show Z-movement of individual bacterial cells before and after antibiotic treatment (FIG. 7A, FIG. 7C and FIG. 7E) paired with PSD of Z-movement of individual bacterial cells before and after antibiotic treatment (FIG. 7B, FIG. 7D and FIG. 7F).
Figure 7B:
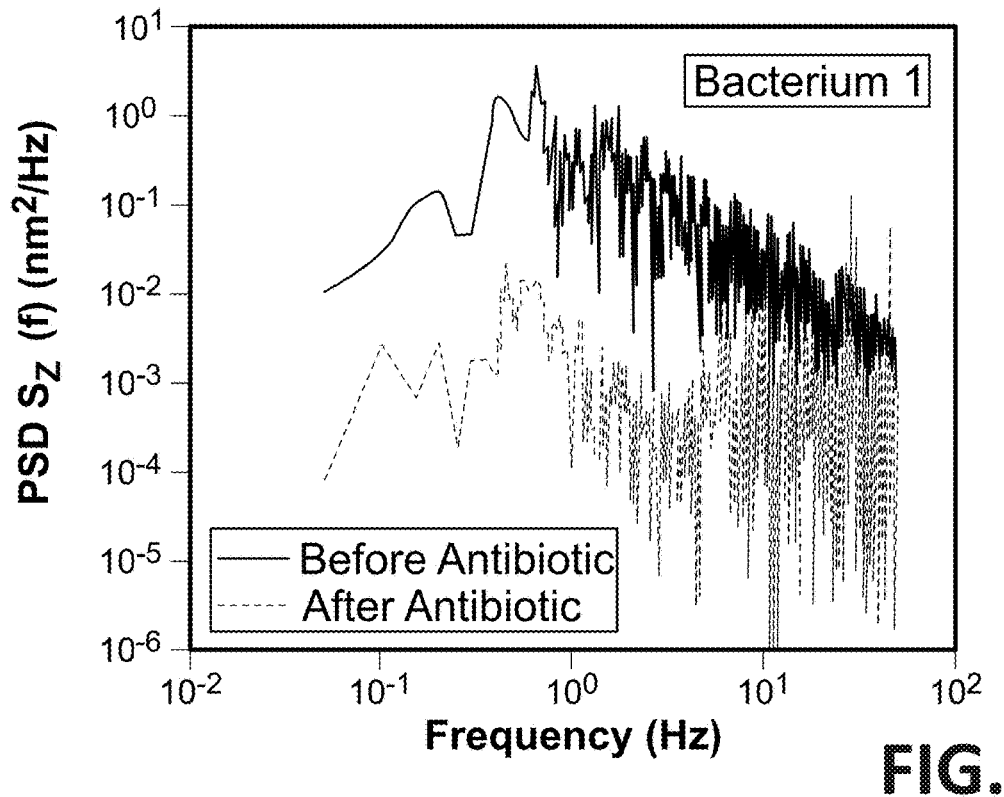
Figure 7C:
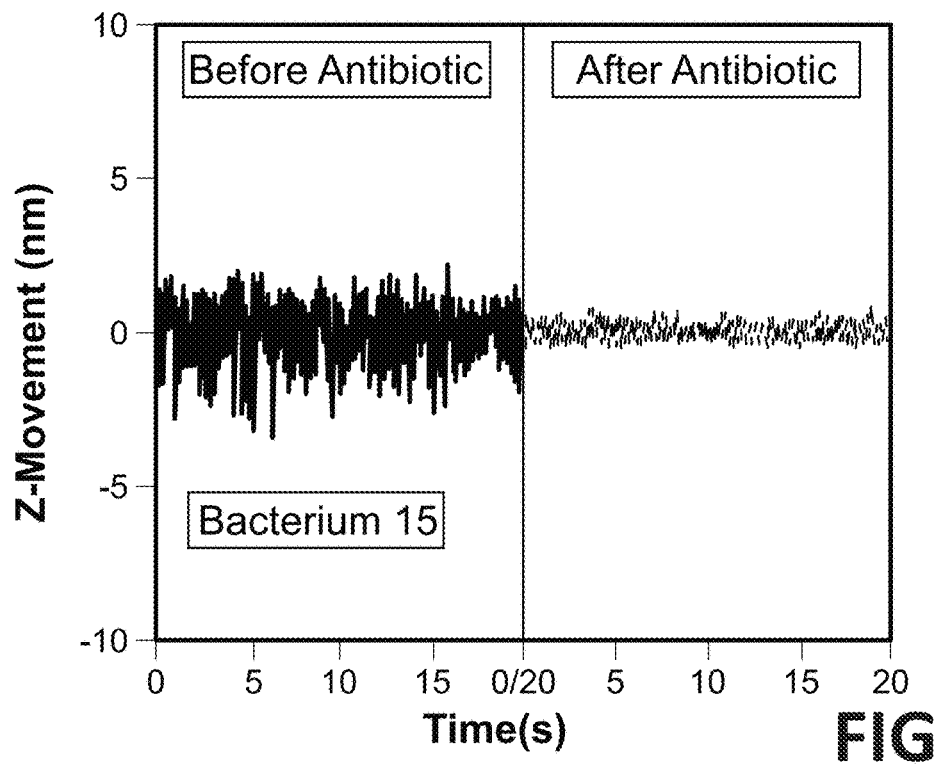
Figure 7D:
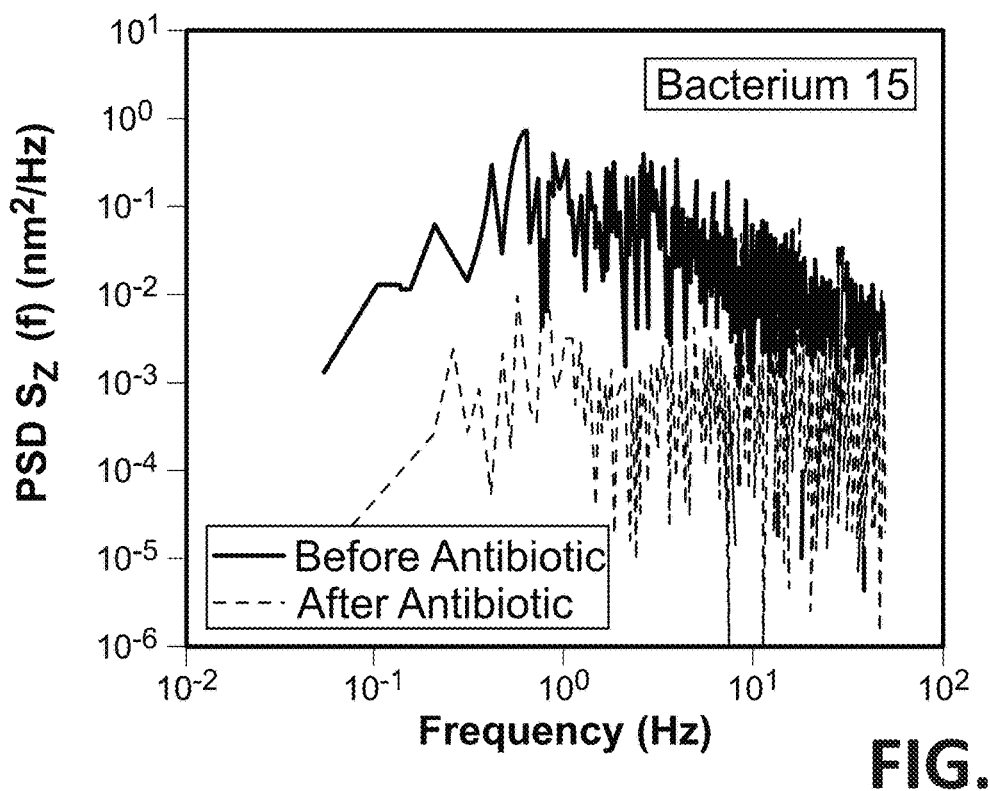
Figure 7E:
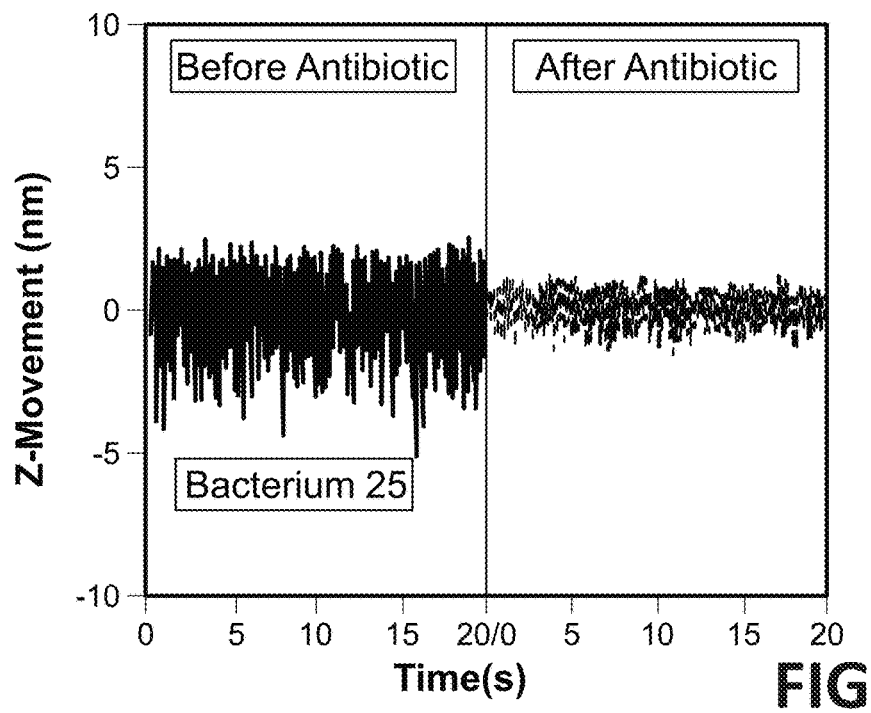

Referring specifically to FIG. 7A, FIG. 7C and FIG. 7E, additional examples of the nanomotion of several bacterial cells before and after antibiotic injection are shown, revealing similar reductions in the nanomotion caused by PMB. FIG. 7A shows an example with bacterium 1. FIG. 7C shows an example with bacterium 15. FIG. 7E shows an example with bacterium 25. The magnitude of the nanomotion varies from cell to cell, both before and after the antibiotic injection. We attribute these variations to bacterial metabolic activities or interactions of individual bacterial cells with antibodies present on the sensor chip.

Figure 7F:
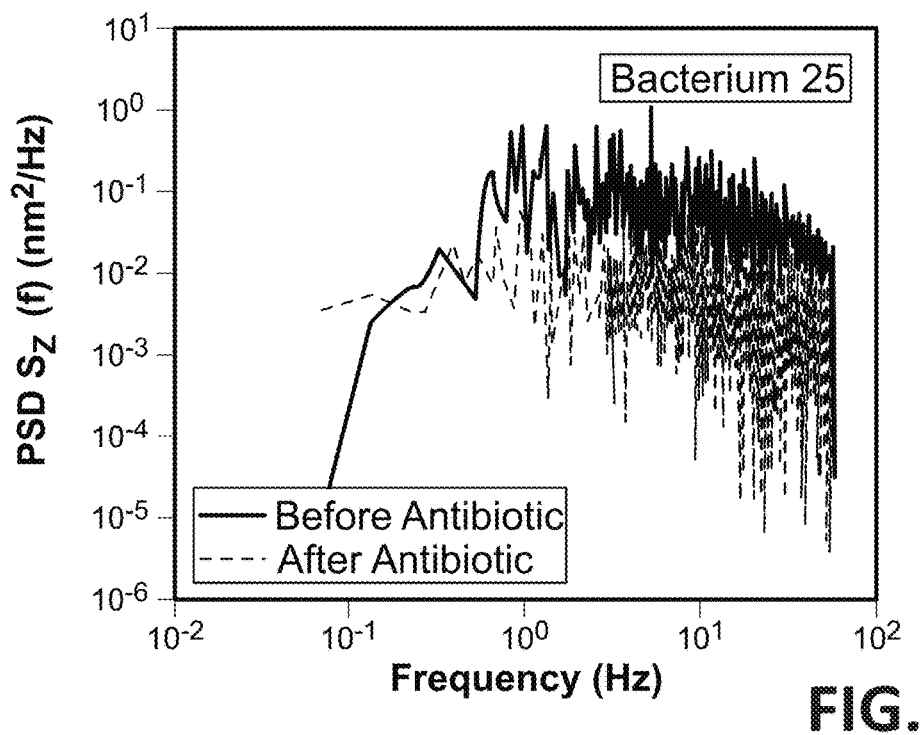

Referring now concurrently to FIG. 7B, FIG. 7D and FIG. 7F, we performed power spectral density (PSD) analysis on the nanomotion. Referring particularly to FIG. 7B, for antibiotic-treated bacterial cells where the Z-movement is small, the PSD shows weak frequency dependence similar to the background noise shown in the lower trace 110. In contrast, the PSD of the live bacterial cells, shown in the upper trace 112, is significantly larger and depends on frequency according to $1/f$ a frequency with $1<a<2$ for frequencies between 1 and 50 Hz. Below 1 Hz, the PSD is not reliable because of the mechanical drift of the optical system, and above 50 Hz, the Z-movement decreases to the background noise level. This PSD feature is similar to that of AFM cantilever defection associated with multiple bacterial cells attached to the cantilever.[54]

Figure 8A:
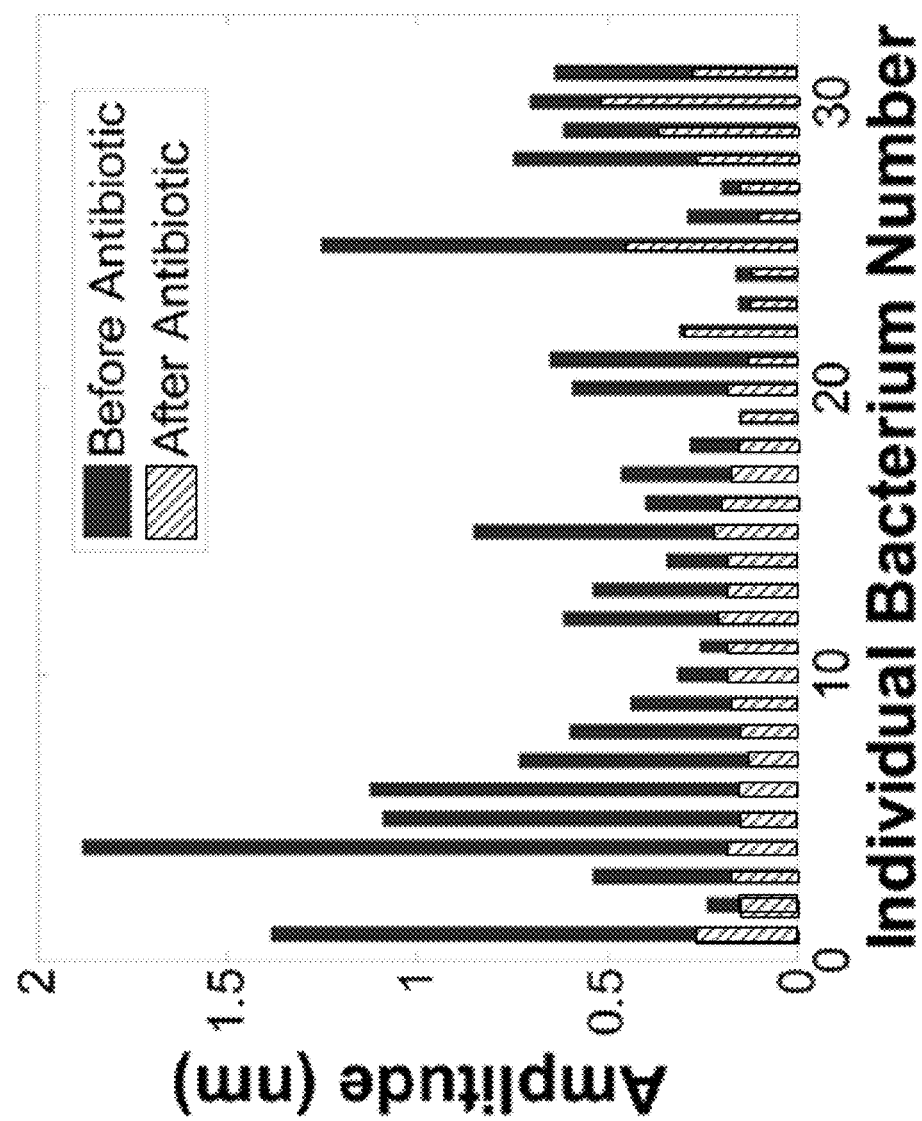
FIG. 8A presents the amplitude histograms of 31 individual bacterial cells before and after antibiotic treatment.

Referring now to FIG. 8A, the amplitude histograms of 31 individual bacterial cells before and after antibiotic treatment are presented. The amplitude has been calculated as the standard deviation of the Z-movement for a period of 20 s. Before antibiotic treatment, there was a large variation in the amplitudes of the nanomotion of the bacterial cells. A few cells exhibited low amplitude nanomotion before antibiotic addition and appeared to be tethered strongly to the surface. After antibiotic treatment, the amplitude of nanomotion for almost all of the bacterial cells decreased. However, for those cells with low initial amplitudes, the decreases in nanomotion after antibiotic treatment are small, which are understandable since the strong tethering restricts motion.

Figure 8B:
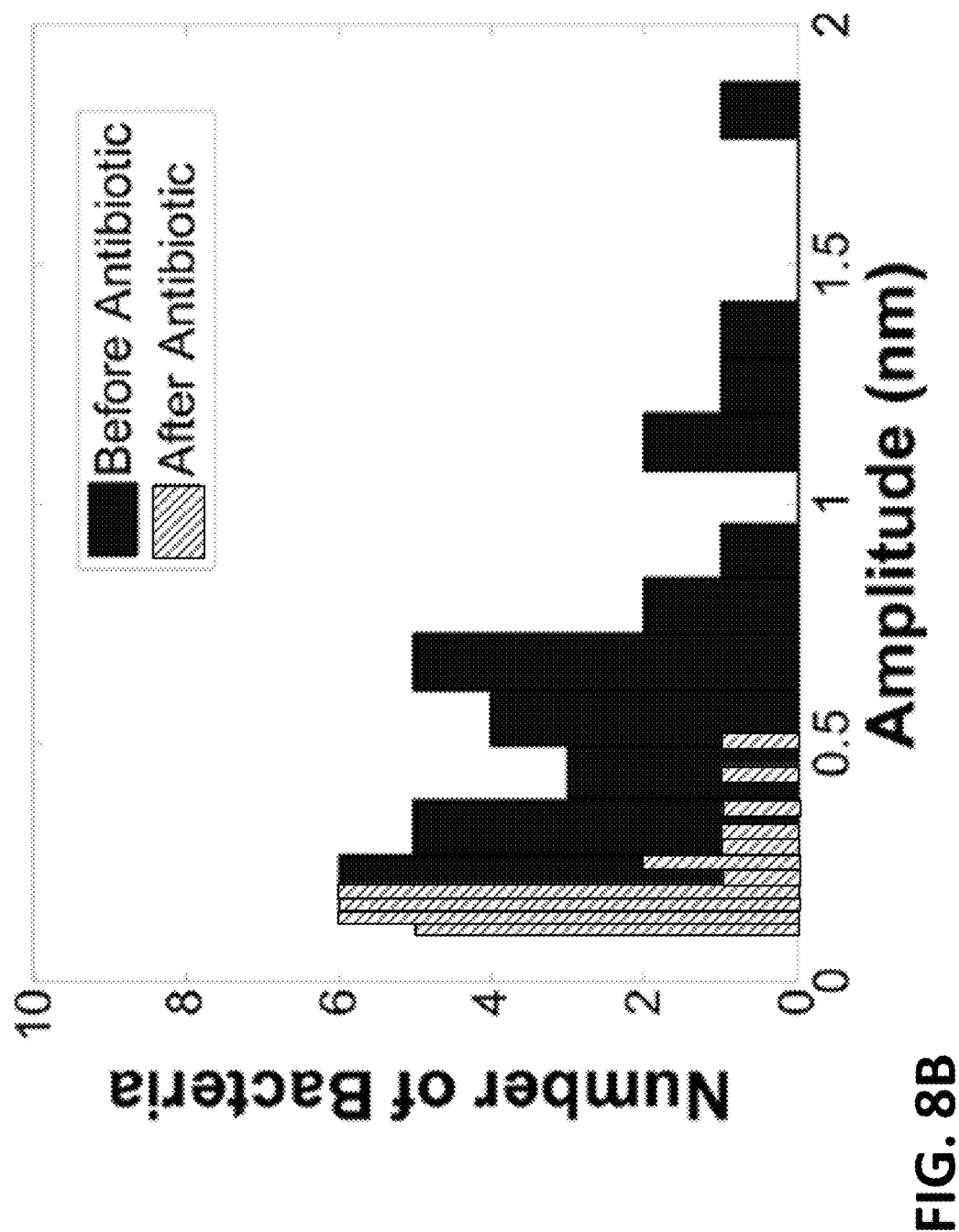
FIG. 8B shows statistical analysis (Student t test) of the mean amplitude value for all bacterial cells before and after antibiotic treatment.

Referring now to FIG. 8B, statistical analysis (Student t test) revealed that the mean amplitude value for all bacterial cells is significantly different before and after antibiotic treatment ($p=2.66\times10-6$).

Figure 12:
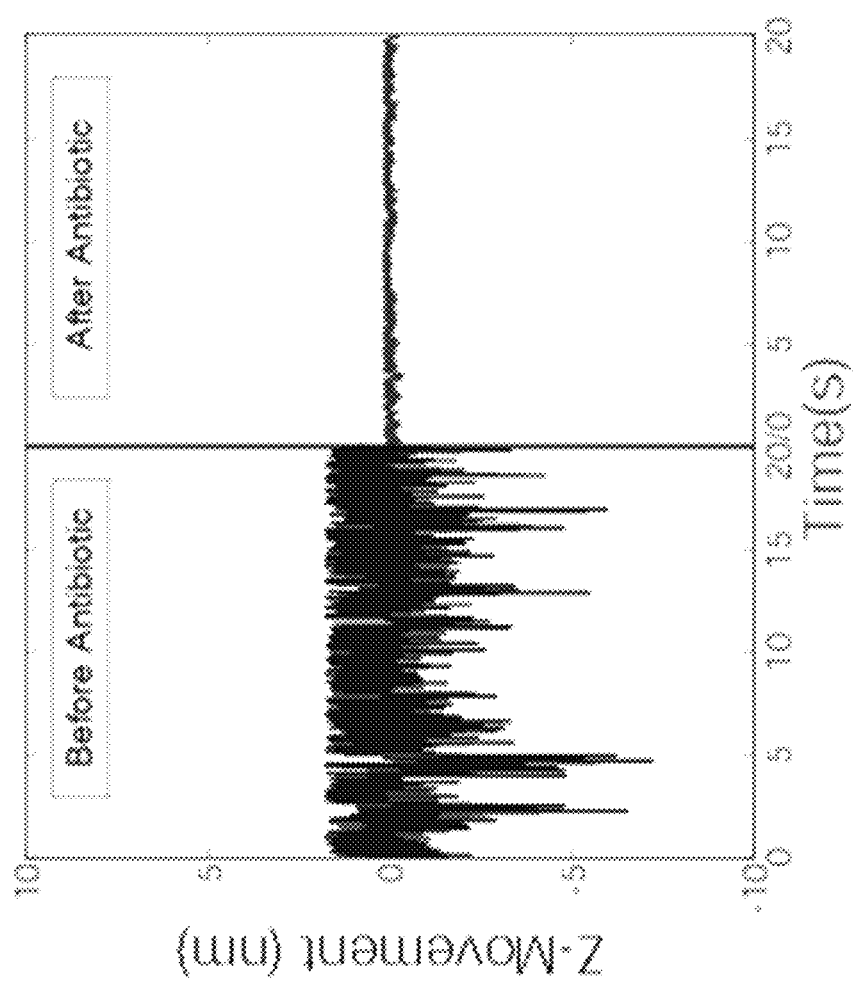
FIG. 12 shows nano-motion changes for UPEC strain on APTES surface.

We further demonstrated the applicability of this technology to UTI infections by extending it to other clinically relevant strains. We immobilized the UPEC strain on the sensor using the (3-aminopropyl)-triethoxysilane (APTES) linker, rather than using the antibody immobilization for the E. coli O157:H7 study described above. We studied the nanomotion changes as antibiotic PMB acted on bacterial cells at a bactericidal concentration of 1 mg/mL. We observed a decrease in bacterial nanomotion when PMB was added indicating that the decrease in nanomotion is specific to antibiotic action. Subsequent overnight culturing of experimental sample in LB medium led to no bacterial growth, thus validating PMB-induced cell death (FIG. 12). We also applied the plasmonic tracking and imaging technology to another antibiotic, streptomycin, and observed a decrease in the nanomotion in the bacterial cells in PBS supplemented with LB media, after adding streptomycin at a bactericidal concentration of 1 mg/mL24,40 (FIG. 12). These experiments indicate that the methods may be used for different bacterial strains and different antibiotics. To fully establish the present method for rapid AST in clinical settings, additional and more comprehensive tests will still be needed in the future.

Figure 9B:
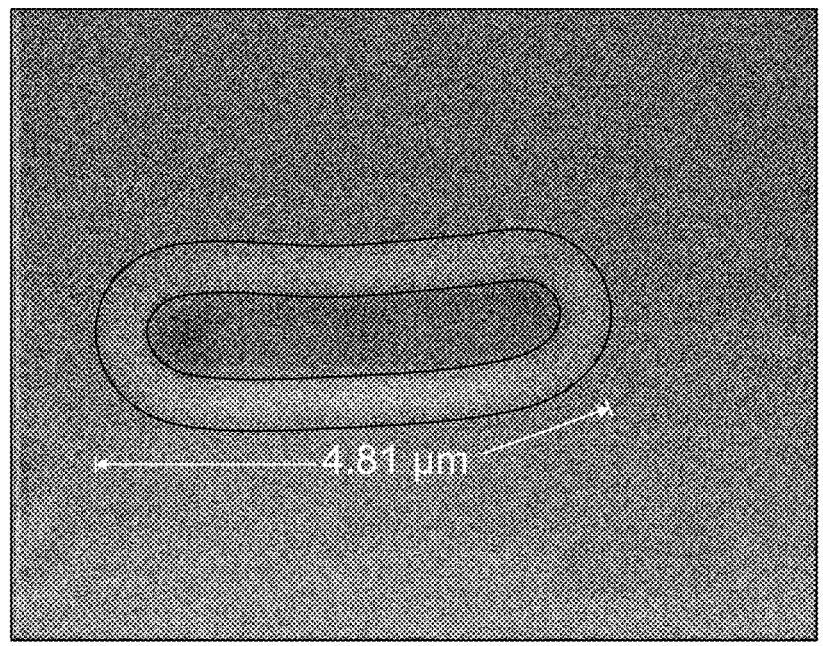
Figure 9C:
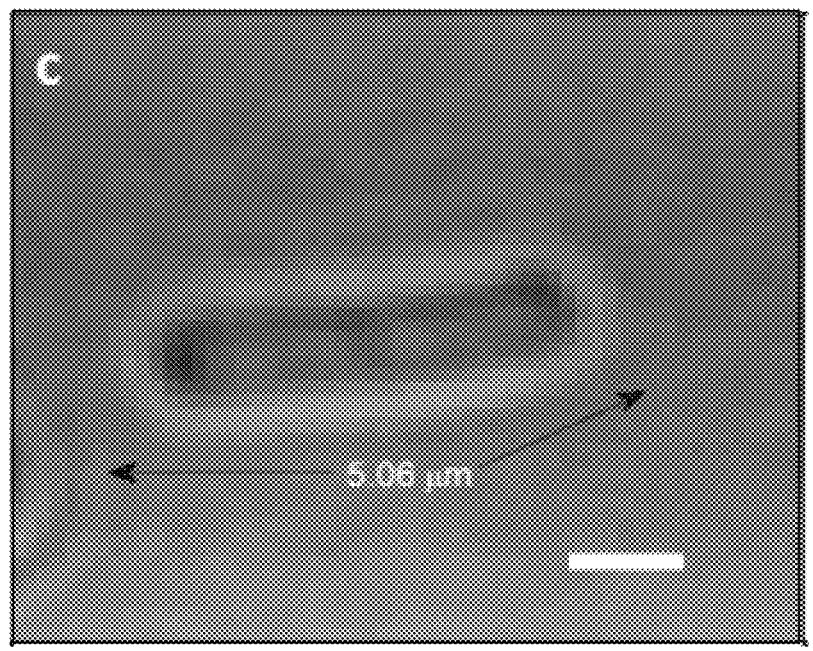

Referring now concurrently to FIG. 9A-FIG. 9C, Z-movement in 1×PBS and LB medium is shown. Specifically referring to FIG. 9A, the left hand trace shows Z-movement of a typical bacterial cell in 1×PBS buffer. The right hand trace shows Z-movement of a typical bacterial cell incubated in LB medium. The Z-movements in both 1×PBS and LB medium are comparable with amplitudes (standard deviation of Z-movement) of 2.31 nm and 2.22 nm, respectively. Pink traces show that detectable motion in the bacterial-free area (system noise) are negligible in both cases. FIG. 9B shows a transmitted image of a bacterial cell in 1×PBS with a recorded length of 4.81 µm. Scale bar (1 µm). FIG. 9C shows a transmitted image of a bacterial cell in LB medium with a recorded length of 5.06 µm. The scale bar for FIG. 9B and FIG. 9C is 1 µm.

Referring now to FIG. 10, Z-movement in 1×PBS and different concentrations of antibiotic is shown. The left trace shows Z-movement of a E. coli O157:H7 cell on the sensor chip in 1×PBS buffer. The middle trace shows that introducing sub-bactericidal concentrations (0.5 µg/ml) of antibiotic PMB does not change the Z-movement. However, introducing the antibiotic at 5× bactericidal concentration (100 µg/m) leads to a large decrease in Z-movement as shown by the right-most trace.

Referring now to FIG. 11 cell death as observed by transmitted images is shown. Bacterial cell 1 before (a1) and after adding antibiotics (a2). The cell length shrinks after adding antibiotics, which indicates possible cell death. Bacterial cell 2 before (b1) and after adding antibiotics (b2). The cell length shrinks after adding antibiotics, which indicates possible cell death. Subsequent culturing experiments confirmed the death of these cells. Scale bar (1 µm).

Referring now to FIG. 12, nano-motion changes for UPEC strain on APTES surface is shown. The left trace shows Z-movement of a bacterial cell of UPEC strain immobilized with APTES on a sensor chip in 1×PBS buffer. The right trace shows Z-movement after injecting 1 mg/ml polymycin B antibiotic. The large decrease in the nanomotion is due to bactericidal action of the antibiotic and subsequent over-night culturing experiments confirmed the death of the bacteria.

Figure 13:
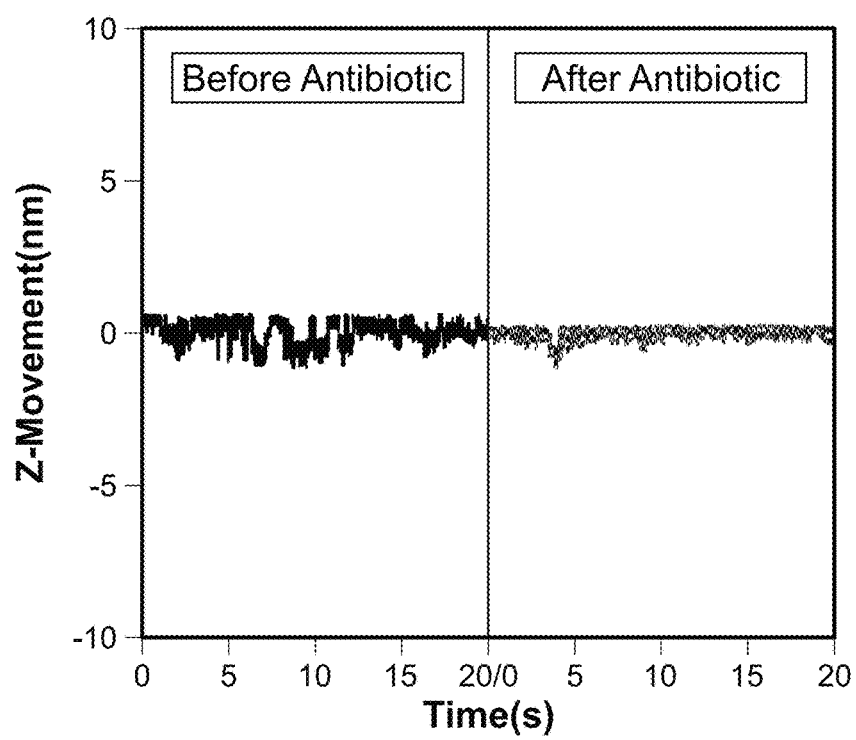
FIG. 13 shows Z-movement for antibiotic Streptomycin for E. coli O157:H7 is shown.

Referring now to FIG. 13, Z-movement for antibiotic Streptomycin for E. coli O157:H7 is shown. The left trace shows Z-movement of a bacterial cell in 0.4×LB media. The right trace shows Z-movement after injecting 1 mg/ml streptomycin antibiotic. The decrease in in nano-motion (Z-movement) correlates to bactericidal action of antibiotic and subsequent over-night culturing experiments confirmed the death of the bacteria.

Methods

Materials.

Lyophilized bacterial pellets of E. coli O157:H7 (ATCC 43888) were purchased from Fisher Scientific. UPEC E. coli strain CFT073 was purchased from ATCC. Affinity-purified goat anti-E. coli O157:H7 IgG polyclonal antibodies were purchased from Kirkegaard and Perry Laboratory, Inc. (Gaithersburg, Md.), suspended in 1 mL of PBS (1×), and stored in aliquots at −20° C. Polymyxin B (PMB) was purchased from Sigma-Aldrich and dissolved in 1×PBS at a stock concentration of 10 mg/mL. PMB was stored in dark at 2-8° C. according to manufacturer's instruction. 1-Mercapto-11-undecyl hexa(ethylene glycol) (PEG) and carboxyl-terminated hexa(ethylene glycol) undecanethiol (PEG-COOH) were purchased from Nano-science Instruments (Phoenix, Ariz.). Other reagents were purchased from Sigma-Aldrich.

Preparation and Growth of Bacteria.

The lyophilized bacteria were suspended in PBS centrifuged at the speed of 50 g for 1 min to pellet the charcoal. The supernatant containing bacteria was collected and centrifuged at 2000 g for 15 min to pellet the bacteria. The bacterial pellet was resuspended in 1 mL of 1×PBS and mixed thoroughly. The final 1 mL of bacteria in PBS solution, after 3 rounds of purification, was collected in small aliquots of 20 μL and frozen at −80° C. adding 5% glycerol. Similarly, E. coli strain CFT073 strain was mixed 5% glycerol and frozen in smaller aliquots at −80° C.

An aliquot of frozen E. coli O157:H7 or E. coli CFT073 strain was thawed and used to inoculate 10 mL of LB medium. E. coli O157:H7 cultures were prepared by diluting the overnight culture (grown at 37° C.) into fresh LB medium to a concentration of 107 colony forming units (cfu)/ml and continuing growth at 37° C. with gentle rotary mixing until the cultures reached mid logarithmic phase of growth. Bacterial cells were collected by centrifugation at 2000 g for 15 min and resuspended in 1 mL of PBS (1×).

Surface Functionalization.

Clean BK7 glass coverslips were coated with 1.5 nm chromium and 47 nm gold and used as SPR sensing chips. The chips were cleaned with deionized water and ethanol for a few times, dried with nitrogen gas, and then cleaned by hydrogen flame. For antibody surface, the cleaned chips were submerged in 1 mM PEG/PEG-COOH ethanol solution and left in the dark for 24 h to coat a PEG/PEG-COOH self-assembled monolayer (SAM) on each chip. For APTES surface, the cleaned chips were submerged in 1 mM PEG solution and left in the dark for 24 h to coat a PEG SAM on the chips. The coated chips were then cleaned again with washes in deionized water and ethanol and subsequently dried with nitrogen gas.

To attach antibodies next, the PEG/PEG-COOH SAM-coated chips were activated with 500 μL of a freshly prepared mixture of 0.1 M NHS and 0.4 M EDC in 1:1 ratio to produce NHS ester receptors, which react with the primary amine groups on the antibodies via an amide bond. Chips with activated PEG/PEG-COOH SAM were cleaned with deionized water and blown dry with nitrogen gas. Polyclonal anti-E. coli O157:H7 IgG antibodies dissolved in 20 mM sodium acetate (NaOAc), pH 5.5 (30 μg/mL), were immediately applied to the NHS/EDC-activated surfaces and incubated for 60-90 min. The antibody-coated chips were again cleaned with deionized water and dried with nitrogen gas prior bacterial cell capture on the PIT setup.

To attach the APTES linker to the sensor surface, the PEG SAM-coated sensors were activated with 100 μL of a freshly prepared 1% APTES in in ethanol (with 5% water) for 2 min. The APTES linked sensor chips were again cleaned with deionized water and dried with nitrogen gas prior bacterial cell capture on the PIT setup.

Plasmonic Imaging and Flow Setup.

The plasmonic imaging setup is based on the Kretschmann configuration with a high numerical aperture objective (NA 1.49) and an inverted microscope (Olympus IX-81) (FIG. 1).32-34 The sensor chip was placed on the objective lens with refractive index matching immersion oil. A 680 nm super luminescent diode (Qphotonics, Ann Arbor, Mich.) was used to excite the SPR images, and a CCD camera (Pike-032B, Allied Vision Technologies, Newbuyport, Mass.) was used to record PIT images.

A FlexiPerm reusable well (SARSTEDT) was mounted on top of the antibody-functionalized gold chip and filled with 500 μL of PBS (1×) buffer. The assembled gold chip was then mounted on top of the plasmonic imaging setup. The incident angle of the light beam was adjusted to the surface plasmon resonance angle, revealing minimal image intensity.

Bacterial Immobilization.

Bacterial cells (20 μL) were added to the sensor chip and tethered onto the sensor surface via noncovalent antibody binding. After a 10-15 min incubation at room temperature, bacterial cells were sufficiently attached to the gold chip. PBS buffer was subsequently flowed over the chip to remove unattached bacterial cells.

Image Collection and Processing.

All plasmonic imaging sequences were collected at 106 fps at a pixel resolution of 640×480. We chose an appropriate exposure time to maximize image intensity and avoid over exposure. Images were recorded in either transmitted or plasmonic imaging mode for various time durations.

Sample Addition.

Multiple sample solutions, including LB medium or PBS, were added to the bacterial cells via a gravity-based multichannel drug perfusion system (Warner Instrument, Hamden, Conn.). The drug perfusion system flew sample solutions over the immobilized bacterial cells at a flow rate of 330 μL/min with the transition time between different flow solutions in the range of 1-2 s. The flow system was stopped and stabilized for 5 min before adding PMB, streptomycin or glucose. To deliver antibiotics, we pipetted small volumes of antibiotics into the Flexiperm well mounted on the microscope.

Data Analyses from Images.

We chose small time durations of about 20 s from the videos to analyze our data and to avoid the influence of focus drift on nanomotion analysis. The images were processed using custom-written MATLAB programs and ImageJ scripts.

Bacterium-Plasmon Surface Z-Distance Tracking and Z-Movement Calculation.

The plasmonic imaging intensity was calculated by obtaining averaged intensity within a fixed area around the bacterial cell, using the bare gold chip regions as a background reference. The Z-distance of the bacterial cell above the plasmon surface was calculated from plasmonic image intensity with the equation: $I_{\Delta z}=I_0 \exp\Delta z/\lambda$.

More specifically, the plasmonic image intensity was calculated by obtaining averaged intensity within a fixed area around the bacterial cell using the bare gold chip regions as reference. The Z-distance of the bacterial cell above the sensor surface was then calculated from the plasmonic image intensity (Iz) with a calibrated curve, given by $$I_z=I_0 \exp(-\Delta z/L),$$

where $I_0$ is a constant, $\Delta z$ is the z displacement of a bacterial cell, and L is the decay constant. The decay constant was determined to be ~95.8 nm.35 Using the above calibration, we calculated the error in the Z-displacement to be about 0.1 nm.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publications are incorporated herein in their entirety by this reference.
1. States, U. Antibiotic resistance threats. (2013). at <cdc.gov/drugresistance/threat-report-2013/pdf/ar-threats-2013-508.pdf>
2. Hancock, R. E. W. The end of an era? Nat. Rev. Drug Discov. 6, 28-28 (2006).
3. Jorgensen, J. H. & Ferraro, M. J. Antimicrobial susceptibility testing: a review of general principles and contemporary practices. Clin. Infect. Dis. 49, 1749-55 (2009).
4. Wiegand, I., Hilpert, K. & Hancock, R. E. W. Agar and broth dilution methods to determine the minimal inhibitory concentration (MIC) of antimicrobial substances. Nat. Protoc. 3, 163-75 (2008).
5. Kinnunen, P. et al. Monitoring the growth and drug susceptibility of individual bacteria using asynchronous magnetic bead rotation sensors. Biosens. Bioelectron. 26, 2751-5 (2011).
6. Sinn, I. et al. Asynchronous magnetic bead rotation microviscometer for rapid, sensitive, and label-free studies of bacterial growth and drug sensitivity. Anal. Chem. 84, 5250-6 (2012).
7. Price, C. S., Kon, S. E. & Metzger, S. Rapid antibiotic susceptibility phenotypic characterization of Staphylococcus aureus using automated microscopy of small numbers of cells. J. Microbiol. Methods 98, 50-8 (2014).
8. Fredborg, M. et al. Real-time optical antimicrobial susceptibility testing. J. Clin. Microbiol. 51, 2047-53 (2013).
9. Longo, G. et al. Rapid detection of bacterial resistance to antibiotics using AFM cantilevers as nanomechanical sensors. Nat. Nanotechnol. 8, 522-6 (2013).
10. Aghayee, S. et al. Combination of fluorescence microscopy and nanomotion detection to characterize bacteria. J. Mol. Recognit. 26, 590-5 (2013).
11. King, A. & King, A. those requiring special handling. 77-80 (2001).
12. Gfeller, K. Y., Nugaeva, N. & Hegner, M. Rapid Biosensor for Detection of Antibiotic-Selective Growth of Escherichia coli Rapid Biosensor for Detection of Antibiotic-Selective Growth of Escherichia coli. 71, (2005).
13. Syal, K. W. W.; Sha. X.; Wan. S. C. H. Y. T. N. Plasmonic imaging of protein interactions with single bacterial cells.
14. Barenfanger, J., Drake, C. & Kacich, G. Clinical and financial benefits of rapid bacterial identification and antimicrobial susceptibility testing. J. Clin. Microbiol. 37, 1415-8 (1999).
15. Wang, W. et al. kinetics of membrane proteins in single living cells. 4, (2012).
16. Wang, W. et al. Single cells and intracellular processes studied by a plasmonic-based electrochemical impedance microscopy. Nat. Chem. 3, 249-55 (2011).
17. Shan, X. et al. Imaging the electrocatalytic activity of single nanoparticles. Nat. Nanotechnol. 7, 668-72 (2012).
18. Wang, S. et al. Label-free imaging, detection, and mass measurement of single viruses by surface plasmon resonance. Proc. Natl. Acad. Sci. U.S.A. 107, 16028-32 (2010).
19. Shan: X. N. Shan, Y. M. Fang, S. P. Wang, Y. Yuan, H.-Y. C. and N. J. T. Detection of charges and molecules with self-assembled nano-oscillators. Nano Lett. (2014).
20. Wang, X., Meier, R. J. & Wolfbeis, O. S. Fluorescent pH-sensitive nanoparticles in an agarose matrix for imaging of bacterial growth and metabolism. Angew. Chem. Int. Ed. Engl. 52, 406-9 (2013).
21. Chattopadhyay, S., Moldovan, R., Yeung, C. & Wu, X. L. Swimming efficiency of bacterium Escherichia coli. Proc. Natl. Acad. Sci. U.S.A. 103, 13712-7 (2006).
22. Kuo, S. C. & Koshland, D. E. Roles of cheY and cheZ gene products in controlling flagellar rotation in bacterial chemotaxis of Escherichia coli. J. Bacteriol. 169, 1307-14 (1987).
23. Weiss, L. E. et al. Engineering motility as a phenotypic response to LuxI/R-dependent quorum sensing in Escherichia coli. Biotechnol. Bioeng. 100, 1251-5 (2008).
24. Mignot, T., Shaevitz, J. W., Hartzell, P. L. & Zusman, D. R. Evidence that focal adhesion complexes power bacterial gliding motility. Science 315, 853-6 (2007).
25. Shi, W. & Lux, R. Focal adhesion: getting a grasp on myxobacterial gliding Iron-sulfur clusters as oxygen-responsive. 3, 205-206 (2007).
26. Topp, S. & Gallivan, J. P. Guiding bacteria with small molecules and RNA. J. Am. Chem. Soc. 129, 6807-11 (2007).
27. Sochacki, K. a, Barns, K. J., Bucki, R. & Weisshaar, J. C. Real-time attack on single Escherichia coli cells by the human antimicrobial peptide LL-37. Proc. Natl. Acad. Sci. U.S.A. 108, E77-81 (2011).
28. Mohan, R. et al. A multiplexed microfluidic platform for rapid antibiotic susceptibility testing. Biosens. Bioelectron. 49, 118-25 (2013).
29. Butler, M. T., Wang, Q. & Harshey, R. M. Cell density and mobility protect swarming bacteria against antibiotics. Proc. Natl. Acad. Sci. U.S.A. 107, 3776-81 (2010).
30. Linares, J. F., Gustafsson, I., Baquero, F. & Martinez, J. L. Antibiotics as intermicrobial signaling agents. 103, (2006).
31. Daniels, R. Surviving the First Hours in Sepsis: Getting the Basics Right (an Intensivist's Perspective). jAntimicrob. Chemother. 2011, 66, 11-23.
32. Wood, K. a.; Angus, D. C. Pharmacoeconomic Implications of New Therapies in Sepsis. PharmacoEconomics 2004, 22, 895-906.
33. Sivanandan, S.; Soraisham, A. S.; Swarnam, K. Choice and Duration of Antimicrobial Therapy for Neonatal Sepsis and Meningitis. Int. jPediatr. 2011, 2011, 1-9.
34. Harbarth, S.; Garbino, J.; Pugin, J.; Romand, J. a.; Lew, D.; Pittet, D. Inappropriate Initial Antimicrobial Therapy and Its Effect on Survival in a Clinical Trial of Immunomodulating Therapy for Severe Sepsis. Am. jMed. 2003, 115, 529-535.
35. Angus, D. C.; van der Poll, T. Severe Sepsis and Septic Shock. N. Engl. jMed. 2013, 369, 840-851.
36. Centers for Disease and Control Prevention. Antibiotic Resistance Threats in the United States, 2013; U.S. Department of Heath and Human Services: Washington, D.C., 2013.
37. Hancock, R. E. W. The End of an Era? Nat. Rev. Drug Discovery 2007, 6, 28-28.
38. Jorgensen, J. H.; Ferraro, M. J. Antimicrobial Susceptibility Testing: A Review of General Principles and Contemporary Practices. Clin. Infect. Dis. 2009, 49, 1749-1755.
39. Wiegand, I.; Hilpert, K.; Hancock, R. E. W. Agar and Broth Dilution Methods to Determine the Minimal Inhibitory Concentration (MIC) of Antimicrobial Substances. Nat. Protoc. 2008, 3, 163-175.
40. Dalgaard, P.; Ross, T.; Kamperman, L.; Neumeyer, K.; McMeekin, T. a. Estimation of Bacterial Growth Rates from Turbidimetric and Viable Count Data. Int. jFood Microbiol. 1994, 23, 391-404.
41. Sinn, I.; Albertson, T.; Kinnunen, P.; Breslauer, D. N.; McNaughton, B. H.; Burns, M. a; Kopelman, R. Asynchronous Magnetic Bead Rotation Microviscometer for Rapid, Sensitive, and Label-Free Studies of Bacterial Growth and Drug Sensitivity. Anal. Chem. 2012, 84, 5250-5256.
42. Kinnunen, P.; Sinn, I.; McNaughton, B. H.; Newton, D. W.; Burns, M. a; Kopelman, R. Monitoring the Growth and Drug Susceptibility of Individual Bacteria Using Asynchronous Magnetic Bead Rotation Sensors. Biosens. Bioelectron. 2011, 26, 2751-2755.
43. Price, C. S.; Kon, S. E.; Metzger, S. Rapid Antibiotic Susceptibility Phenotypic Characterization of *Staphylococcus Aureus* Using Automated Microscopy of Small Numbers of Cells. jMicrobiol. Methods 2014, 98, 50-58.
44. Choi, J.; Jung, Y.-G.; Kim, J.; Kim, S.; Jung, U.; Na, H.; Kwon, S. Rapid Antibiotic Susceptibility Testing by Tracking Single Cell Growth in a Microfluidic Agarose Channel System. Lab Chip 2013, 13, 280-287.
45. Fredborg, M.; Andersen, K. R.; Jørgensen, E.; Droce, A.; Olesen, T.; Jensen, B. B.; Rosenvinge, F. S.; Sondergaard, T. E. Real-Time Optical Antimicrobial Susceptibility Testing. jClin. Microbiol. 2013, 51, 2047-2053.
46. Mohan, R.; Mukherjee, A.; Sevgen, S. E.; Sanpitakseree, C.; Lee, J.; Schroeder, C. M.; Kenis, P. J. a. A Multiplexed Microfluidic Platform for Rapid Antibiotic Susceptibility Testing. Biosens. Bioelectron. 2013, 49, 118-125.
47. Lu, Y.; Gao, J.; Zhang, D. D.; Gau, V.; Liao, J. C.; Wong, P. K. Single Cell Antimicrobial Susceptibility Testing by Confined Micro-channels and Electrokinetic Loading. Anal. Chem. 2013, 85, 3971-3976.
48. Wang, X.; Meier, R. J.; Wolfbeis, O. S. Fluorescent pH-Sensitive Nanoparticles in an Agarose Matrix for Imaging of Bacterial Growth and Metabolism. Angew. Chem., Int. Ed. 2013, 52, 406-409.
49. Metzger, S.; Frobel, R. a.; Dunne, W. M. Rapid Simultaneous Identification and Quantitation of *Staphylococcus Aureus* and Pseudomonas Aeruginosa Directly from Bronchoalveolar Lavage Specimens Using Automated Microscopy. Diagn. Microbiol. Infect. Dis. 2014, 79, 160-165.
50. Choi, J.; Yoo, J.; Lee, M.; Kim, E.; Lee, J. S.; Lee, S.; Joo, S.; Song, S. H.; Kim, E.; Lee, J. C.; et al. A Rapid Antimicrobial Susceptibility Test Based on Single-Cell Morphological Analysis. Sci. Transl. Med. 2014, 6, 267ra174.
51. King, A. Recommendations for Susceptibility Tests on Fastidious Organisms and Those Requiring Special Handling. J. Antimicrob. Chemother. 2001, 48, 77-80.
52. Longo, G.; Alonso-Sarduy, L.; Rio, L. M.; Bizzini, a; Trampuz, a; Notz, J.; Dietler, G.; Kasas, S. Rapid Detection of Bacterial Resistance to Antibiotics Using AFM Cantilevers as Nanomechanical Sensors. Nat. Nanotechnol. 2013, 8, 522-526.
53. Aghayee, S.; Benadiba, C.; Notz, J.; Kasas, S.; Dietler, G.; Longo, G. Combination of Fluorescence Microscopy and Nanomotion Detection to Characterize Bacteria. J. Mol. Recognit. 2013, 26, 590-595.
54. Lissandrello, C.; Inci, F.; Francom, M.; Paul, M. R.; Demirci, U.; Ekinci, K. L. Nanomechanical Motion of *Escherichia Coli* Adhered to a Surface. Appl. Phys. Lett. 2014, 105, 113701.
55. Kasas, S.; Simone, F.; Benadiba, C.; Maillard, C.; Stupar, P.; Tournu, H. Detecting Nanoscale Vibrations as Signature of Life. Proc. Natl. Acad. Sci. U.S.A. 2015, 112, 378-381.
56. Song, L.; Sjollema, J.; Sharma, P. K.; Kaper, H. J.; van der Mei, H. C.; Busscher, H. J. Nanoscopic Vibrations of Bacteria with Different Cell-Wall Properties Adhering to Surfaces under Flow and Static Conditions. ACS Nano 2014, 8, 8457-8467.
57. Syal, K.; Wang, W.; Shan, X.; Wang, S.; Chen, H. Y.; Tao, N. Plasmonic Imaging of Protein Interactions with Single Bacterial Cells. Biosens. Bioelectron. 2015, 63, 131-137.
58. Wang, W.; Foley, K.; Shan, X.; Wang, S.; Eaton, S.; Nagaraj, V. J.; Wiktor, P.; Patel, U.; Tao, N. Single Cells and Intracellular Processes Studied by a Plasmonic-Based Electrochemical Impedance Microscopy. Nat. Chem. 2011, 3, 249-255.
59. Besser, R. E.; Griffin, P. M.; Slutsker, L. *Escherichia Coli* O157:H7 Gastroenteritis and the Hemolytic Uremic Syndrome: An Emerging Infectious Disease. Annu. Rev. Med. 1999, 50, 355-367.
60. Daugelavičius, R.; Bakiené, E.; Bamford, D. H. Stages of Polymyxin B Interaction with the *Escherichia Coli* Cell Envelope. Antimicrob. Agents Chemother. 2000, 44, 2969-2978.
61. Flores-Mireles, A. L.; Walker, J. N.; Caparon, M.; Hultgren, S. J. Urinary Tract Infections: Epidemiology, Mechanisms of Infection and Treatment Options. Nat. Rev. Microbiol. 2015, 13, 269-284.
62. Wang, W.; Yang, Y.; Wang, S.; Nagaraj, V. J.; Liu, Q.; Wu, J.; Tao, N. Label-Free Measuring and Mapping of Binding Kinetics of Membrane Proteins in Single Living Cells. Nat. Chem. 2012, 4, 846-873.
63. Wang, S.; Shan, X.; Patel, U.; Huang, X.; Lu, J.; Li, J.; Tao, N. Label-Free Imaging, Detection, and Mass Measurement of Single Viruses by Surface Plasmon Resonance. Proc. Natl. Acad. Sci. U.S.A. 2010, 107, 16028-16032.
64. Shan, X.; DíeZ-Pérez, I.; Wang, L.; Wiktor, P.; Gu, Y.; Zhang, L.; Wang, W.; Lu, J.; Wang, S.; Gong, Q.; et al. Imaging the Electrocatalytic Activity of Single Nanoparticles. Nat. Nanotechnol. 2012, 7, 668-672.
65. Yang, Y.; Yu, H.; Shan, X.; Wang, W.; Liu, X.; Wang, S.; Tao, N. Label-Free Tracking of Single Organelle Transportation in Cells with Nanometer Precision Using a Plasmonic Imaging Technique. Small 2015, 11, 2878-2884.
66. Shan, X.; Fang, Y.; Wang, S.; Guan, Y.; Chen, H. Y.; Tao, N. Detection of Charges and Molecules with Self-Assembled Nano-Oscillators. Nano Lett. 2014, 14, 4151-4157.
67. Parry, B. R.; Surovtsev, I. V.; Cabeen, M. T.; O'Hern, C. S.; Dufresne, E. R.; Jacobs-Wagner, C. The Bacterial Cytoplasm Has Glass-like Properties and Is Fluidized by Metabolic Activity. Cell 2014, 156, 183-194.
68. Zhang, Y.; Rock, C. O. Membrane Lipid Homeostasis in Bacteria. Nat. Rev. Microbiol. 2008, 6, 222-233.
69. Sochacki, K. a; Barns, K. J.; Bucki, R.; Weisshaar, J. C. Real-Time Attack on Single *Escherichia Coli* Cells by the Human Antimicrobial Peptide LL-37. Proc. Natl. Acad. Sci. U.S.A. 2011, 108, E77-E81.

70. Ocampo, P. S.; Lázár, V.; Papp, B.; Arnoldini, M.; Zur Wiesch, P. A.; Busa-Fekete, R.; Fekete, G.; Pál, C.; Ackermann, M.; Bonhoeffer, S. Antagonism between Bacteriostatic and Bactericidal Antibiotics Is Prevalent. Antimicrob. Agents Chemother. 2014, 58, 4573-4582.

What is claimed is:

1. A method for antibiotic susceptibility testing using plasmonic imaging for bacterial cells comprising:
    providing a plasmonic imaging and tracking (PIT) system including an inverted microscope lens, a light source, a metallic coated slide, a mirror and a detector;
    attaching tethering molecules to the metallic coated surface;
    populating the metallic coated surface with bacteria;
    activating the PIT system;
    imaging the bacteria using the PIT system;
    tracking a first set of 3D motion values of the bacteria;
    adding an antibiotic to the metallic coated surface;
    tracking a second set of 3D motion values of the bacteria in the presence of the antibiotic; and
    comparing the first and second 3D motion values to determine changes in the 3D motion of the bacteria after addition of the antibiotic.

2. The method of claim 1 wherein attaching tethering molecules comprises attaching tethering molecules with an affinity to a bacterial cell under investigation.

3. The method of claim 2 wherein attaching tethering molecules comprises attaching antibodies.

4. The method of claim 1 wherein populating the metallic coated surface with a bacteria comprises populating the metallic coated surface with a bacteria selected from the group consisting of *E. coli* and *S. aureus*.

5. The method of claim 1 wherein attaching tethering molecules comprises attaching tethering molecules including anti-*E. coli* antibodies.

6. The method of claim 1 wherein attaching tethering molecules comprises attaching tethering molecules selected from the group consisting of cell-adhesion promoting substances, poly-lysine, and agar matrix.

7. The method of claim 1 wherein populating the metallic coated surface with the bacteria comprises tethering the bacteria within a distance of less than five hundred nm from the metallic coated surface.

8. The method of claim 1 wherein tracking a first set of 3D motion values comprises:
    extracting an image intensity change from the plasmonic image that is free of noise;
    processing a plasmonic image of a bacterial cell where the plasmonic image includes a bright spot with a parabolic shaped tail;
    tracking bacteria XY-motion by detecting the bright spot at the vertex of the parabolic shaped tail; and
    tracking bacteria Z-motion by detecting substantially perpendicular motion relative to the metallic coated surface.

9. The method of claim 8 wherein tracking the XY-motion comprises using a curve fitting algorithm.

10. The method of claim 9 wherein the curve-fitting algorithm is selected from the group consisting of Gaussian fitting, elliptical fitting, and spatial averaging.

11. The method of claim 8 wherein extracting an image intensity change from the plasmonic image that is free of noise comprises transforming the plasmonic image into K-space using Fourier transforms to produce a two-ring image.

12. A method for antibiotic susceptibility testing using plasmonic imaging for individual bacterial cells comprising:
    providing a plasmonic imaging and tracking (PIT) system including an inverted microscope lens, a light source, a metallic coated slide, a mirror and a detector;
    attaching tethering molecules to the metallic coated surface;
    populating the metallic coated surface with individual bacterial cells;
    activating the PIT system;
    imaging, using the PIT system, the individual bacterial cells;
    tracking a first set of 3D motion values of each of the individual bacterial cells;
    adding an antibiotic to the metallic coated surface;
    tracking a second set of 3D motion values of each of the individual bacterial cells in the presence of the antibiotic; and
    comparing the first and second 3D motion values to determine changes in the 3D motion of each of the individual bacterial cells after addition of the antibiotic.

* * * * *